US011072624B2

(12) United States Patent
Huang

(10) Patent No.: US 11,072,624 B2
(45) Date of Patent: Jul. 27, 2021

(54) SYNTHESIS OF NUCLEOSIDE 5'-TRIPHOSPHATES AND THEIR DERIVATIVES

(75) Inventor: Zhen Huang, Marietta, GA (US)

(73) Assignee: SENA RESEARCH, INCORPORATED, Marietta, GA (US)

( * ) Notice: Subject to any disclaimer, the term of this patent is extended or adjusted under 35 U.S.C. 154(b) by 0 days.

(21) Appl. No.: 13/817,820

(22) PCT Filed: Aug. 19, 2011

(86) PCT No.: PCT/US2011/048485
§ 371 (c)(1),
(2), (4) Date: Feb. 19, 2013

(87) PCT Pub. No.: WO2012/024625
PCT Pub. Date: Feb. 23, 2012

(65) Prior Publication Data
US 2013/0158249 A1    Jun. 20, 2013

Related U.S. Application Data

(60) Provisional application No. 61/375,560, filed on Aug. 20, 2010, provisional application No. 61/375,992, filed on Aug. 23, 2010.

(51) Int. Cl.
| | |
|---|---|
| *C07H 1/04* | (2006.01) |
| *C07H 19/10* | (2006.01) |
| *C07H 19/20* | (2006.01) |
| *C07H 21/00* | (2006.01) |

(52) U.S. Cl.
CPC .............. *C07H 1/04* (2013.01); *C07H 19/10* (2013.01); *C07H 19/20* (2013.01); *C07H 21/00* (2013.01)

(58) Field of Classification Search
CPC .......... C07H 19/10; C07H 1/04; C07H 21/00; C07H 19/20
See application file for complete search history.

(56) References Cited

U.S. PATENT DOCUMENTS

| | | | | |
|---|---|---|---|---|
| 7,592,446 B2 * | 9/2009 | Huang | ........................... | 536/28.1 |
| 7,982,030 B2 * | 7/2011 | Huang | ........................... | 536/27.21 |
| 8,354,524 B2 * | 1/2013 | Huang | ........................... | 536/26.8 |
| 8,394,934 B2 * | 3/2013 | Huang et al. | ................. | 536/1.11 |
| 8,809,357 B2 * | 8/2014 | Huang | ........................... | 514/274 |

OTHER PUBLICATIONS

Ludwig et al., "Rapid and Efficient Synthesis of Nucleoside 5'-O-(1-Thiophosphates), 5'-Triphosphates, and 2',3'-Cyclophosphorothioates Using 2-Chloro-4H-1,3,2-benzodioxaphosphorin-4-one," Journal of Organic Chemistry, 54(3), 631-635 (1989).*

Brandt et al., "Efficient Substrate Cleavage Catalyzed by Hammerhead Ribozymes Derivatized with Selenium for X-Ray Crystallography," Biochemistry, 45(29), 8972-8977 (Jun. 6, 2006).*

Carrasco et al., "Efficient Enzymatic Synthesis of Phosphoroselenoate RNA by Using Adenosine 5'-(a-P-Seleno)triphosphate," Angewandte Chemie International Edition, 45, 94-97 (2006).*

Han et al., "Synthesis of Boronate, Selenoate, and Thioate Analogs of AZTp4A and Ap4A," Tetrahedron, 65, 7015-7920 (Aug. 6, 2009).*

Misiura et al., "Synthesis of Nucleoside (alpha)-Thiotriphosphates via an Oxathiaphospholane Approach," Organic Letters, 7(11), 2217-2220 (May 6, 2005).*

(V) Misiura et al., "Synthesis of Nucleoside (alpha)-Thiotriphosphates via an Oxathiaphospholane Approach," Organic Letters, 7(11) ,2217-2220 (May 6, 2005).*

(W) He et al., Syntheisis and Separation of Diastereoisomers of Ribonucleoside 5'-(a-P-Borano)triphosphates, Journal of Organic Chemistry,m 63(17), 5769-5773 (1998).*

Ahmadibeni et al., "Synthesis of Nucleoside Mono-, Di-, and Triphosphoramidates from Solid-Phase cycloSaligenyl Phosphitylating Reagents," Organic Letters 2009, vol. 11, No. 10, pp. 2157-2160.

Aketani et M., "Syntheses and Structure-Activity Relationships of Nonnatural β-C-Nucleoside 5'-Triphosphates Bearing an Aromatic Nucleobase with Phenolic Hydroxy Groups: Inhibitory Activities against DNA Polymerases," J. Med. Chem. 2002, 45, pp. 5594-5603.

Asada et al., "Continuous ATP Regeneration Utilizing Glycolysis and Kinase Systems of Yeast," Agric. Biol. Chem. 1978, 42(8), pp. 1533-1538.

August et al., "Initial Studies on the Cellular Pharmacology of 3'-Deoxythymidin-2'-ene (d4T): A Potent and Selective Inhibitor of Human Immunodeficiency Virus," Biochemical Pharmacology 1988, vol. 37, No. 23, pp. 4419-4422.

(Continued)

Primary Examiner — Lawrence E Crane
(74) Attorney, Agent, or Firm — Merchant & Gould P.C.

(57) ABSTRACT

Disclosed are nucleoside 5'-triphosphates modified at the α, (β, and/or γ phosphate to substitute one or more of the phosphate oxygen atoms with a borano, seleno, and/or thio group. Derivatives and pharmaceutically acceptable salts are also contemplated herein. Also disclosed are processes for preparing nucleoside 5'-triphosphates. Non-limiting, exemplary processes can include first reacting salicyl phosphorochloridite with a pyrophosphate reagent to provide P2, P3-dioxo-P1-(salicyl) cyclotriphosphite, and then reacting P2, P3-dioxo-P1-(salicyl) cyclotriphosphite with a nucleoside, followed by oxidation of the nucleoside-phosphite intermediate and hydrolysis to form the modified nucleoside 5'-triphosphate. Nucleoside 5'-triphosphates can be useful in nucleic acid replication, transcription, and translation. Processes disclosed herein are not limited to nucleoside 5'-triphosphates having a native base moiety, such as 9-adeninyl, 1-cytosinyl, 9-guaninyl, 1-thyminyl, or 1-uracilyl, and are also effective for the preparation of nucleoside 5'-triphosphates having a modified nucleobase or unnatural nucleobase.

16 Claims, 8 Drawing Sheets
Specification includes a Sequence Listing.

(56) References Cited

OTHER PUBLICATIONS

Baddiley et al., "Nucleotides. Part II. A Synthesis of Adenosine Triphosphate," J. Chem. Soc. London 1949, pp. 582-586.
Burgess et al., "Syntheses of Nucleoside Triphosphates," Chem. Rev. 2000, 100, pp. 2047-2059.
Eckstein, "Nucleoside Phosphorothioates," Ann. Rev. Biochem. 1985, 54, pp. 367-402.
Elia et al., "In vitro efficacy of ribavirin against canine distemper virus," Antiviral Research 2008, 77, pp. 108113.
Fiske et al., "Phosphorus Compounds of Muscle and Liver," Science 1929, 70, pp. 381-382.
Gish et al., "DNA and RNA Sequence Determination Based on Phosphorothioate Chemistry," Science 1988, 240, pp. 1520-1522.
Golubeva et al., "New Nucleoside Analogues and Their 5'-Triphosphates: Synthesis and Biological Properties," Moscow University Chemistry Bulletin 2008, vol. 63, No. 2, pp. 89-93.
Harvey et al., "Small-Scale Preparation of 5'-Nucleotides and Analogs by Carrot Phosphotransferase," Analytical Biochemistry 1970, 36, pp. 413-421.
Horhota et al., "Glycerol Nucleoside Triphosphates: Synthesis and Polymerase Substrate Activities," Organic Letters 2006, vol. 8, No. 23, pp. 5345-5347.
Jansen et al. "Facile Small Scale Synthesis of Nucleoside 5'-Phosphate Mixtures," Nucleosides, Nucleotides and Nucleic Acids 2010, 29, pp. 14-26, 14 pages.
Krzyzanowska et al., "A Convenient Synthesis of 2'-Deoxyribonucleoside 5'-(a-P-Borano)triphosphates," Tetrahedron 1998, 54, pp. 5119-5128.
Lin et al., "Synthesis of a novel triphosphate analogue: nucleoside a-P-borano, a-P-thiotriphosphate," Chemical Communications 2000, pp. 2115-2116.
Lohmann, "Nachweis von Atomtrümmern aus Aluminium mit dem Hoffmannschen Elektrometer," Naturwissenschaften 1929, 17, pp. 624-625.
Mandal et al., "Gene Regulation by Riboswitches," Nature Reviews Molecular Cell Biology 2004, 5, pp. 451-463.
Maxam et al., "A new method for sequencing DNA," Proc. Natl. Acad. Sci. Usa 1977, vol. 74, No. 2, pp. 560-564.
McManus et al., "Gene Silencing in Mammals by Small Interfering RNAs," Nature Reviews Genetics 2002, vol. 3, pp. 737-747.
Mitsuya et al., "Molecular Targets for AIDS Therapy," Science 1990, vol. 249, pp. 1533-1544.
Satoh, "Über Die Hydrolyse Der Adenosinfriphosphorsaure Durch Phosphomonoesterase Und Pyrophosphatase," The Journal of Biochemistry 1935, vol. 21, No. 1, pp. 19-36.
Storz, "An Expanding Universe of Noncoding RNAs," Science 2002, vol. 296, pp. 1260-1263, 5 pages.
Sun et al., "One-Pot Synthesis of Nucleoside 5'-Triphosphates from Nucleoside 5'-H-Phosphonates," Organic Letters 2008, vol. 10, No. 9, pp. 1703-1706.
Walseth et al., "The Enzymatic Preparation of [α-$^{32}$P]Nucleoside Triphosphates, Cyclic [$^{32}$P]AMP, and Cyclic [$^{32}$P]GMP," Biochimica et Biophysica Acta 1979, 526, pp. 11-31.
Warnecke et al., "New and efficient Synthesis of Nucleoside Polyphosphates and Nucleoside Monophosphate Sugars," Nucleic Acids Symposium Series 2008, No. 52, pp. 583-584.
Wu et al., "A Combination Chemical and Enzymatic Approach for the Preparation of Azole Carboxamide Nucleoside Triphosphate," J. Org. Chem 2003, 68, pp. 3860-3865.
Wu et al., "A Novel Method for the Preparation of Nucleoside Triphosphates from Activated Nucleoside Phosphoramidates," Organic Letters 2004, vol. 6, No. 13, pp. 2257-2260.
Yoshikawa et al., "A Novel Method for Phosphorylation of Nucleosides to 5'-Nucleotides," Tetrahedron Letters 1967, No. 50, pp. 5065-5068.
S. Bag et al.. Journal of Nucleic Acids, 2012, vol. 2012, 1-2.
M. Chawla, Nucleic Acids Research, 2015, 43:14, 6714-6729.

* cited by examiner

A
5'-d-GCG TAA TAC GAC TCA CTA TA G-3' (SEQ. ID NO: 1)
3'-d-GCATTATGCTGAGTGATATCGTCTGGACTACTCCGGCTTTCCGGCTTTGCATGT-5'
(SEQ ID NO: 2)

B Standards

| | | | | | | | | | | | | |
|---|---|---|---|---|---|---|---|---|---|---|---|---|
| dATP | + | + | − | Test dATP | + | + | + | + | + | + | Test dATP | − |
| dCTP | + | + | + | + | − | Test dCTP | + | + | + | + | Test dCTP | − |
| dGTP | + | + | + | + | + | + | − | Test dGTP | + | + | Test dGTP | − |
| TTP | + | + | + | + | + | + | + | + | − | Test TTP | Test TTP | − |
| Kf- | − | + | + | + | + | + | + | + | + | + | + | − |
| Lane: | 1 | 2 | 3 | 4 | 5 | 6 | 7 | 8 | 9 | 10 | 11 | 12 |

SEQUENCE LISTING

<160> NUMBER OF SEQ ID NOS: 7

<210> SEQ ID NO 1
<211> LENGTH: 21
<212> TYPE: DNA
<213> ORGANISM: unknown
<220> FEATURE:
<223> OTHER INFORMATION: mammal

<400> SEQUENCE: 1
gcgtaatacg actcactata g                                     21

<210> SEQ ID NO 2
<211> LENGTH: 54
<212> TYPE: DNA
<213> ORGANISM: unknown
<220> FEATURE:
<223> OTHER INFORMATION: mammal

<400> SEQUENCE: 2
acatgcaaag ccggaaagcc ggagtagtcc agacgatatc actcagcata atgc    54

<210> SEQ ID NO 3
<211> LENGTH: 55
<212> TYPE: DNA
<213> ORGANISM: Artificial Sequence
<220> FEATURE:
<223> OTHER INFORMATION: DNA fragment with NTPalphaSe analogs
<220> FEATURE:
<221> NAME/KEY: modified_base
<222> LOCATION: (21)..(55)
<223> OTHER INFORMATION: NTPalphaSe analogs

<400> SEQUENCE: 3
gcgtaatacg actcactata gcatacctga tgaggccgaa aggccgaaac gtaca    55

<210> SEQ ID NO 4
<211> LENGTH: 35
<212> TYPE: RNA
<213> ORGANISM: Artificial Sequence
<220> FEATURE:
<223> OTHER INFORMATION: RNA sequence modified with alpha-selenated UTP
<220> FEATURE:
<221> NAME/KEY: modified_base
<222> LOCATION: (8)..(8)
<223> OTHER INFORMATION: UTPalphaSe
<220> FEATURE:
<221> NAME/KEY: modified_base
<222> LOCATION: (11)..(11)
<223> OTHER INFORMATION: UTPalphaSe
<220> FEATURE:
<221> NAME/KEY: modified_base
<222> LOCATION: (31)..(31)
<223> OTHER INFORMATION: UTPalphaSe

<400> SEQUENCE: 4
ggcaaccuga ugaggccgaa aggccgaaac guaca                       35

<210> SEQ ID NO 5
<211> LENGTH: 55

```
<212> TYPE: DNA
<213> ORGANISM: unknown
<220> FEATURE:
<223> OTHER INFORMATION: mammal

<400> SEQUENCE: 5
acatgcaaag ccggaaagcc ggagtagtcc agacgatatc actcagcata atgcg          55

<210> SEQ ID NO 6
<211> LENGTH: 69
<212> TYPE: RNA
<213> ORGANISM: unknown
<220> FEATURE:
<223> OTHER INFORMATION: hammerhead

<400> SEQUENCE: 6
gggagcccug ucaccggaug ugcuuuccgg ucugaugagu ccgugaggac gaaacagggc     60
ucccgaauu                                                            69

<210> SEQ ID NO 7
<211> LENGTH: 89
<212> TYPE: DNA
<213> ORGANISM: unknown
<220> FEATURE:
<223> OTHER INFORMATION: hammerhead

<400> SEQUENCE: 7
aattcgggag ccctgtttcg tcctcacgga ctcatcagac cggaaagcac atccggtgac    60
agggctccct atagtgagtc gtattacgc                                      89
```

SYNTHESIS OF NUCLEOSIDE 5'-TRIPHOSPHATES AND THEIR DERIVATIVES

CROSS-REFERENCE TO RELATED APPLICATIONS

This application is a U.S. National Stage Application under 35 U.S.C. § 371 of International Application No. PCT/US2011/048485 filed Aug. 19, 2011, which claims benefit of U.S. Provisional Application No. 61/375,560 filed Aug. 20, 2010 and U.S. Provisional Application No. 61/375,992 filed Aug. 23, 2010, the contents of which are all incorporated herein in their entirety by this reference.

REFERENCE TO AN ELECTRONIC SEQUENCE LISTING

The contents of the electronic sequence listing (0001us-wo_Sequence_Listing.txt; Size: 2,052 bytes; and Date of Creation: Mar. 6, 2018 May 30, 2018) are herein incorporated by reference in their entirety.

BACKGROUND

Natural nucleoside 5'-triphosphates (NTPs and dNTPs) are the basic building blocks for the synthesis of nucleic acids (RNA and/or DNA) and are utilized in DNA replication, transcription and translation [G. Storz, Science 2002, 296, 1260-3; M. T. McManus, P. A. Sharp, Nat Rev Genet 2002, 3, 737-47; M. Mandal, R. R. Breaker, Nat Rev Mol Cell Biol 2004, 5, 451-63]. Nucleic acids participate in many important biological systems including genetic information storage, gene expression, catalysis, and numerous other biochemical processes [G. Gish, F. Eckstein, Science 1988, 240, 1520-2; F. Eckstein, Annu Rev Biochem 1985, 54, 367-402 10.1146/annurev.bi.54.070185. 002055]. Nucleoside 5'-triphosphates have many important therapeutic and diagnostic applications [N. A. Golubeva, Ivanov, A. V., Vanov, M. A., Batyunina, O. A., Shipitsyn, A. V. Tunitskaya, V. L. and Alexandrova, L. A., Mosco University Chemistry Bulletin 2008, 63, 89-93]. Analogs of these nucleoside triphosphates are prepared and are particularly useful as DNA sequencing tools [A. M. Maxam, W. Gilbert, Proc Natl Acad Sci USA 1977, 74, 560-4], active metabolites of drugs [G. Elia, C. Belloli, F. Cirone, M. S. Lucente, M. Caruso, V. Martella, N. Decaro, C. Buonavoglia, P. Ormas, Antiviral Res 2008, 77, 108-13; E. M. August, M. E. Marongiu, T. S. Lin, W. H. Prusoff, Biochem Pharmacol 1988, 37, 4419-22], mechanistic probes, polymerase chain reaction and for general analytical and therapeutic research [H. Mitsuya, R. Yarchoan, S. Broder, Science 1990, 249, 1533-44].

Naturally occurring NTPs and dNTPs have been isolated from cells decades ago [K. Lohmann, Naturwiss 1929, 17, 624-625; C. H. Fiske, Y. Subbarow, Science 1929, 70, 381-382; K. Lohmann, Biochem. Z. 1931, 233, 460-466; T. Satoh, J. Biochem. Jpn. 1935, 2, 19-36]. Furthermore, enzymatic syntheses of nucleoside triphosphates has been employed where triphosphates have been synthesized intracellularly and extracellularly from nucleosides in the presence of kinases [C. L. Harvey, E. M. Clericuzio, A. L. Nussbaum, Anal Biochem 1970, 36, 413-21; M. Asada, Nakanishi, K., Agric. Biol. Chem. 1978, 42, 1533-1538; T. F. Walseth, R. A. Johnson, Biochim Biophys Acta 1979, 562, 11-31]. Because of the vital role nucleotides play in biological processes, it prompted chemists to chemically synthesize triphosphates to further explore these processes and have a better understanding of their roles in nucleic acids. It is worth mentioning that nucleoside triphosphates serve as substrates for DNA polymerases where the incorporation into DNA strands is performed with extremely high accuracy in a template-directed manner.

Chemical synthesis of nucleoside triphosphate was achieved a long time ago [J. Baddiley, Michelson, A. M. and Todd, A. R., J. Chem. Soc. London 1949, 582-586]. However, these procedures required the appropriate protection of the starting materials and hence, all intermediates to avoid undesired products. The purification process is usually tedious, rendering the protocols very laborious and time consuming. One traditional and popular method used for the preparation of a wide range of triphosphates is the procedure developed by Ludwig and Eckstein [J. a. E. Ludwig, F. (1989) Rapid and Efficient Synthesis of Nucleoside 5'-0-(1-, -. T. a. Thiotriphosphates), 3'-Cyclophosphorothioates Using 2-Chloro-4H-1,3,2-, benzodioxaphosphorin-4-one. J. Org. Chem., 631-635., J. Org. Chem. 1989, 54, 631-635]. Their strategy employs the use of 2-chloro-4H-1,3,2-benzodioxaphosphorin-4-one (salicyl phosphorochloridite) as the phosphitylating reagent. This reagent can undergo multiple nucleophilic displacement reactions. The common strategy is to at first form the $P^2,P^3$-dioxo-$P^1$-5'-nucleosidylcyclotriphosphite followed by the addition of pyrophosphate, then oxidation and finally hydrolysis to form the nucleoside 5'-triphosphate. This strategy usually requires protection of the sugar moiety such as the use of an acid labile group; however, this one-pot strategy is not applicable to all derivatives [K. Burgess, D. Cook, Chem Rev 2000, 100, 2047-60]. There are a host of other synthetic strategies [Y. Ahmadibeni, R. K. Tiwari, G. Sun, K. Parang, Org Lett 2009, 11, 2157-60 10.1021%1900320r; W. Wu, C. L. Freel Meyers, R. F. Borch, Org Lett 2004, 6, 2257-60 10.1021%1049267j; Q. Sun, J. P. Edathil, R. Wu, E. D. Smidansky, C. E. Cameron, B. R. Peterson, Org Lett 2008, 10, 1703-6 10.1021/ol8003029; S. Warnecke, C. Meier, Nucleic Acids Symp Ser (Oxf) 2008, 583-4 nrn295 [pii] 10.1093/nass/nrn295; A. T. Horhota, J. W. Szostak, L. W. McLaughlin, Org Lett 2006, 8, 5345-7 10.1021%1062232u; M. Yoshikawa, T. Kato, T. Takenishi, Tetrahedron Lett 1967, 50, 5065-8; S. Aketani, K. Tanaka, K. Yamamoto, A. Ishihama, H. Cao, A. Tengeiji, S. Hiraoka, M. Shiro, M. Shionoya, J Med Chem 2002, 45, 5594-603 µm020193w [pii]; R. S. J. H. R. J. H. S. J. H. Beijnen, Nucleosides, Nucleotides and Nucleic Acids 2009, 29, 14-26] developed to prepare nucleoside triphosphates, but in some scenarios, the procedures usually require protection of the sugar moiety, longer synthetic route, difficulty in purification and isolation of the desired product, and low yield [K. Burgess, D. Cook, Chem Rev 2000, 100, 2047-60; W. Wu, D. E. Bergstrom, V. J. Davisson, J Org Chem 2003, 68, 3860-5 10.1021/jo020745i].

Therefore, there is a continuing need to develop alternative processes of preparation of nucleoside triphosphate (i.e., native 2'-deoxynucleoside 5'-triphosphates) with fewer, simple and convenient synthetic steps, improved scalability, more simple, convenient and efficient isolation and purification of the product, easier handling, better yields, less reaction time, less consumption of starting materials, enhanced safety, reduced contamination to the environment, and reduced costs associated with the process.

Further, in the last decade, the knowledge about RNA and RNA-related molecules has been greatly advanced [Sioud, M. and P. O. Iversen (2005). "Ribozymes, DNAzymes and small interfering RNAs as therapeutics." Curr Drug Targets 6(6): 647-653; Makarova, J. A. and D. A. Kramerov (2007).

"Noncoding RNAs." *Biochemistry (Mosc)* 72(11): 1161-1178]. Except tRNA, rRNA and catalytic RNAs, more functional RNA molecules have been discovered and the diversity is staggering. The recent findings include riboswitch, microRNA, siRNA, snRNA, piRNA, rasiRNA and tasiRNA, the list of which could be even longer [Gilbert, S. D., R. K. Montange, et al. (2006). "Structural studies of the purine and SAM binding riboswitches." *Cold Spring Harb Sump Quant Biol* 71: 259-268; Kato, M. and F. J. Slack (2008). "microRNAs: small molecules with big roles—*C. elegans* to human cancer." *Biol Cell* 100(2): 71-81; Jady, B. E. and T. Kiss (2001). "A small nucleolar guide RNA functions both in 2'-O-ribose methylation and pseudouridylation of the U5 spliceosomal RNA." *Embo J* 20(3): 541-551; Aravin, A. A., G. J. Hannon, et al. (2007). "The Piwi-piRNA pathway provides an adaptive defense in the transposon arms race." *Science* 318(5851): 761-764; Klenov, M. S., S. A. Lavrov, et al. (2007). "Repeat-associated siRNAs cause chromatin silencing of retrotransposons in the *Drosophila melanogaster* germline." *Nucleic Acids Res* 35(16): 5430-5438; Tabara, H., M. Sarkissian, et al. (1999). "The rde-1 gene, RNA interference, and transposon silencing in *C. elegans*." *Cell* 99(2): 123-132; Vazquez, F., H. Vaucheret, et al. (2004). "Endogenous trans-acting siRNAs regulate the accumulation of *Arabidopsis* mRNAs." *Mol Cell* 16(1): 69-79]. A wide range of biomolecules and biological events have been reported to be under the sophisticated regulation of these noncoding RNAs. The field of RNA and RNA-related molecules calls for more detailed structure and functions studies.

For structure and function studies of nucleic acids, various derivatization tools (e.g., selenium, sulfur or borane derivative) is a facilitator for crystallography by replacement of selected oxygen atoms in DNA or RNA. Compared with traditional halogen derivatization, selenium-, sulfur- or borane-derivatization is more stable to X-ray exposure. Therefore, there is a continuing need to develop proceses of preparation of selenium-, sulfur- or borane-derivatization of RNA and/or DNA, as well as their application for structure and function studies.

SUMMARY

Disclosed are compounds of nucleoside 5'-triphosphates of formula (I), or derivatives thereof, or pharmaceutically acceptable salts of said nucleoside 5'-triphosphates or said derivatives,

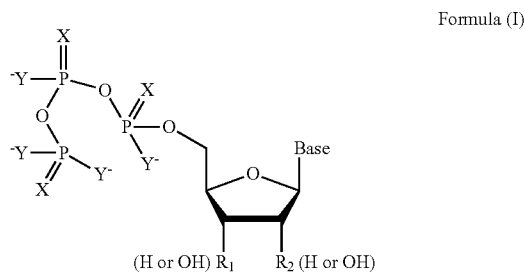

Formula (I)

wherein the Base of formula (I) is Adenine (A), Cytosine (C), Guanine (G), Thymine (T), Uracil (U), modified nucleobase or unnatural nucleobase; $R_1$ is H or OH, $R_2$ is H or OH, X is independently selected from the group consisting of O, S and Se; and Y is independently selected from the group consisting of O, B (borano, or $BH_3$), S, and Se. Also disclosed are processes of preparing said compounds of formula (I), said process comprising steps according to Scheme A:

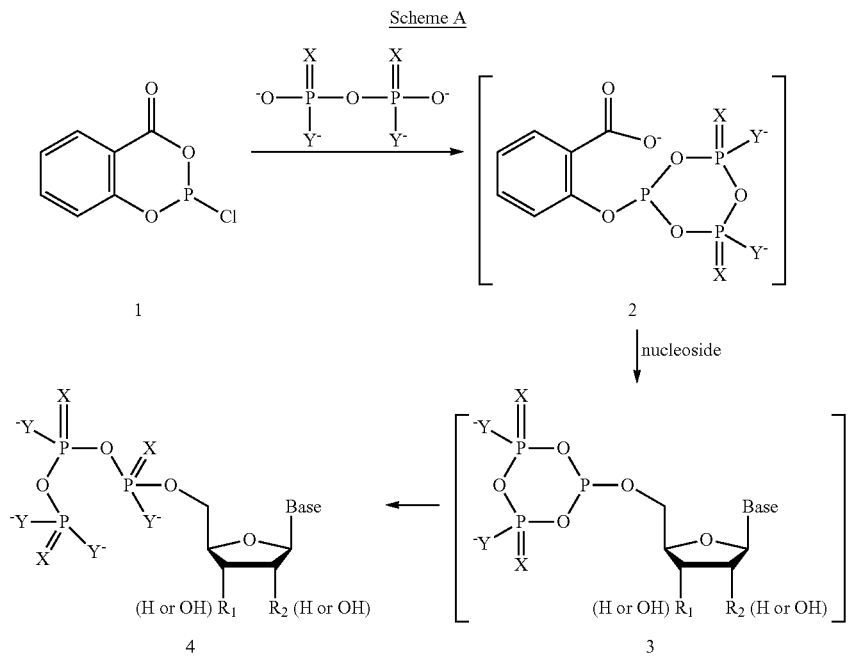

wherein in step (a), salicyl phosphorochloridite 1 or a derivative of said salicyl phosphorochloridite 1 is reacted with an suitable pyrophosphate reagent or a derivative of said pyrophosphate reagent under a suitable solvent and suitable temperature to provide a cyclic phosphite intermediate 2 (P2,P3-dioxo-P1-(salicyl)cyclotriphosphite), and then said intermediate 2 is reacted with a nucleoside under a suitable solvent and suitable temperature to provide an intermediate 3 ($P^2,P^3$-dioxo-$P^1$-5'-(nucleosidyl-5'-O-)cyclotriphosphite); and in step (b), said intermediate 3 is converted to product 4 (nucleoside 5'-triphosphate) via oxidation with suitable oxidative reagent and then hydrolysis with or without a suitable base.

BRIEF DESCRIPTION OF THE DRAWINGS

The accompanying drawings, which are incorporated in and constitute a part of this specification, illustrate several forms and together with the description illustrate the disclosed compounds and methods.

DETAILED DESCRIPTION

Figure 1:
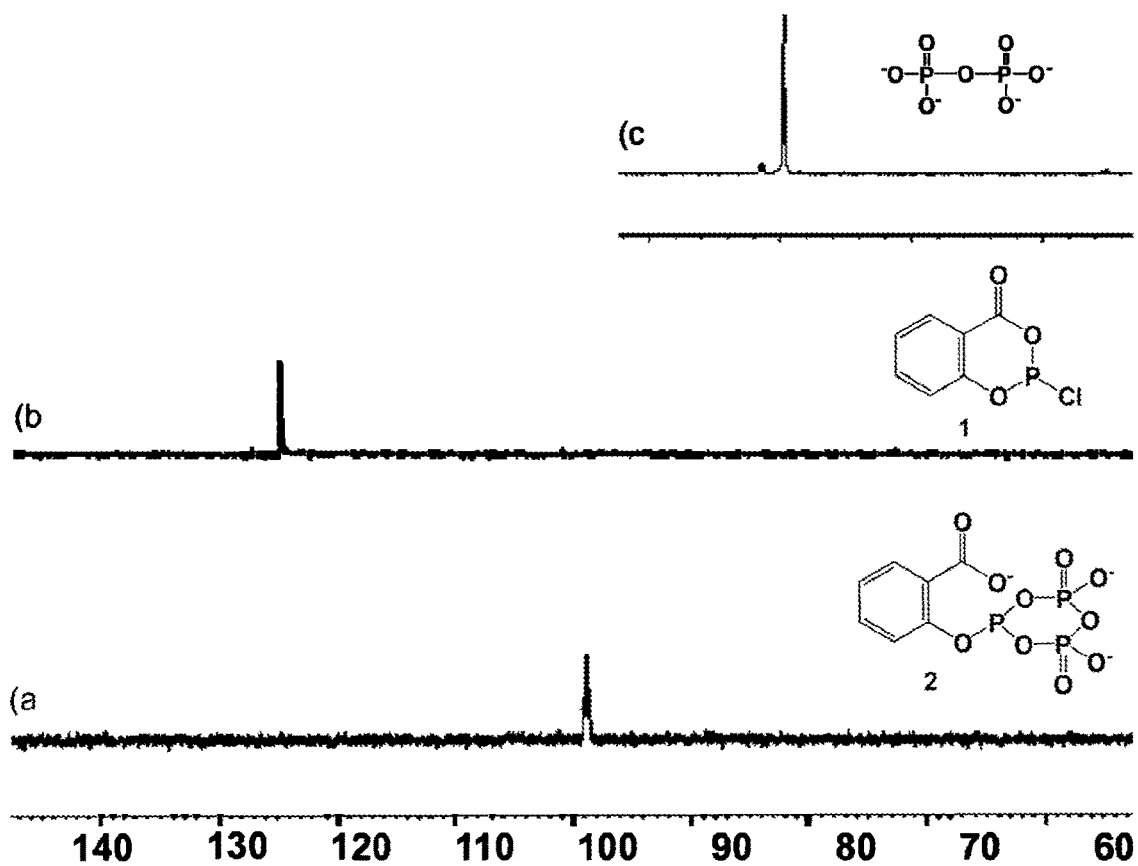
FIG. 1 shows $^{31}$P NMR (DMF $d_7$) of phosphitylating reagent a at room temperature. The starting reagents: b. salicyl phosphorochloridite and c. tributyl ammonium pyrophosphate.

Before the present compounds, compositions, articles, devices, systems, and/or methods are disclosed and described, it is to be understood that they are not limited to specific synthetic methods or specific treatment methods unless otherwise specified, or to particular reagents unless otherwise specified, as such may, of course, vary. It is also to be understood that the terminology used herein is for the purpose of describing particular forms only and is not intended to be limiting.

Compositions

Disclosed are compounds of nucleoside 5'-triphosphates of formula (I), or derivatives thereof, or pharmaceutically acceptable salts of said nucleoside 5'-triphosphates or said derivatives,

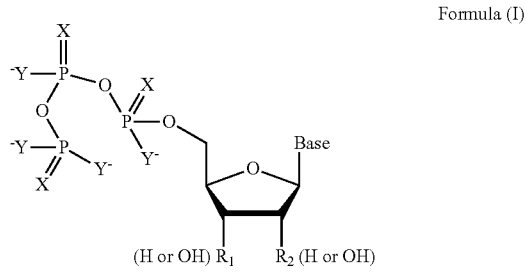

Formula (I)

wherein the Base of formula (I) is Adenine (A), Cytosine (C), Guanine (G), Thymine (T), Uracil (U), modified nucleobase or unnatural nucleobase; $R_1$ is H or OH, $R_2$ is H or OH, X is independently selected from the group consisting of O, S and Se; and Y is independently selected from the group consisting of O, B (borano, or $BH_3$), S, and Se.

In some forms, the disclosed compounds are compounds wherein said compound is a beta-modified nucleoside 5'-triphosphate selected from the group consisting of nucleoside 5'-(β-P-thiotriphosphates), nucleoside 5'-(β-P-selenotriphosphates) and nucleoside 5'-(β-P-boranotriphosphates). In other forms, the disclosed compounds are compounds wherein said compound is a gamma-modified nucleoside 5'-triphosphate selected from the group consisting of nucleoside 5'-(γ-P-thiotriphosphates), nucleoside 5'-(γ-P-selenotriphosphates) and nucleoside 5'-(γ-P-boranotriphosphates).

In some other forms, the disclosed compounds are compounds wherein said compound is an alpha-, beta-modified nucleoside 5'-triphosphate. In some other forms, the disclosed compounds are compounds wherein said compound is a beta-, gamma-modified nucleoside 5'-triphosphate. In some other forms, the disclosed compounds are compounds wherein said compound is an alpha-, gamma-modified nucleoside 5'-triphosphate. In some other forms, the disclosed compounds are compounds wherein said compound is an alpha-, beta-, gamma-modified nucleoside 5'-triphosphate.

In some forms, the disclosed compounds are compounds wherein said compound is nucleoside 5'-(α-P-seleno, β-P-selenotriphosphates). In some other forms, the disclosed compounds are compounds wherein said compound is nucleoside 5'-(α-P-seleno, γ-P-selenotriphosphates). In some other forms, the disclosed compounds are compounds wherein said compound is nucleoside 5'-(β-P-seleno, γ-P-selenotriphosphates). In some other forms, the disclosed compounds are compounds wherein said compound is nucleoside 5'-(α-P-seleno, β-P-seleno, γ-P-selenotriphosphates). In some forms, disclosed are compositions comprising any one or more of the above-disclosed compounds.

Methods

Disclosed are processes of preparing a nucleoside 5'-triphosphate of formula (I), or a derivative thereof, or a pharmaceutically acceptable salt of said nucleoside 5'-triphosphate or said derivative,

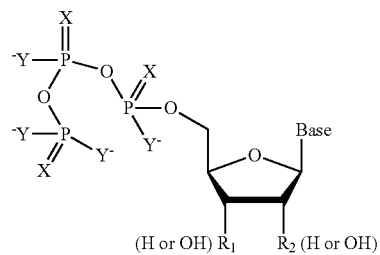

Formula (I)

(H or OH) R₁    R₂ (H or OH)

wherein the Base of formula (I) is Adenine (A), Cytosine (C), Guanine (G), Thymine (T), Uracil (U), modified nucleobase or unnatural nucleobase; $R_1$ is H or OH, $R_2$ is H or OH, X is independently selected from the group consisting of O, S and Se; and Y is independently selected from the group consisting of O, B (borano, or $BH_3$), S, and Se; and said process comprising steps according to Scheme A:

with an suitable pyrophosphate reagent or a derivative of said pyrophosphate reagent under a suitable solvent and suitable temperature to provide a cyclic phosphite intermediate 2 (P2,P3-dioxo-P1-(salicyl)cyclotriphosphite), and then said intermediate 2 is reacted with a nucleoside under a suitable solvent and suitable temperature to provide an intermediate 3 (P²,P³-dioxo-P¹-5'-(nucleosidyl-5'-O-)cyclotriphosphite); and in step (b), said intermediate 3 is converted to product 4 (nucleoside 5'-triphosphate) via oxidation with suitable oxidative reagent and then hydrolysis with or without a suitable base.

In some forms, the disclosed processes are processes wherein said nucleoside 5'-triphosphate is a 2'deoxynucleoside 5'-triphosphate (dNTP) of formula (II):

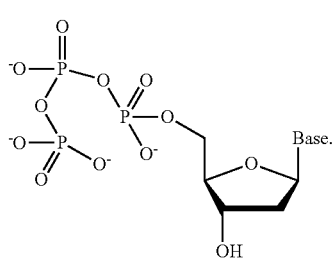

Formula (II)

In some other forms, the disclosed processes are processes wherein in the conversion of starting material 1 to said intermediate 2 of step (a), said suitable pyrophosphate reagent is tributyl ammonium pyrophosphate, said suitable solvent is DMF, and said suitable temperature is from about room temperature to about 100° C.; and wherein in the conversion of said intermediate 2 to said intermediate 3 of step (a), said suitable solvent is DMF and said suitable Scheme A

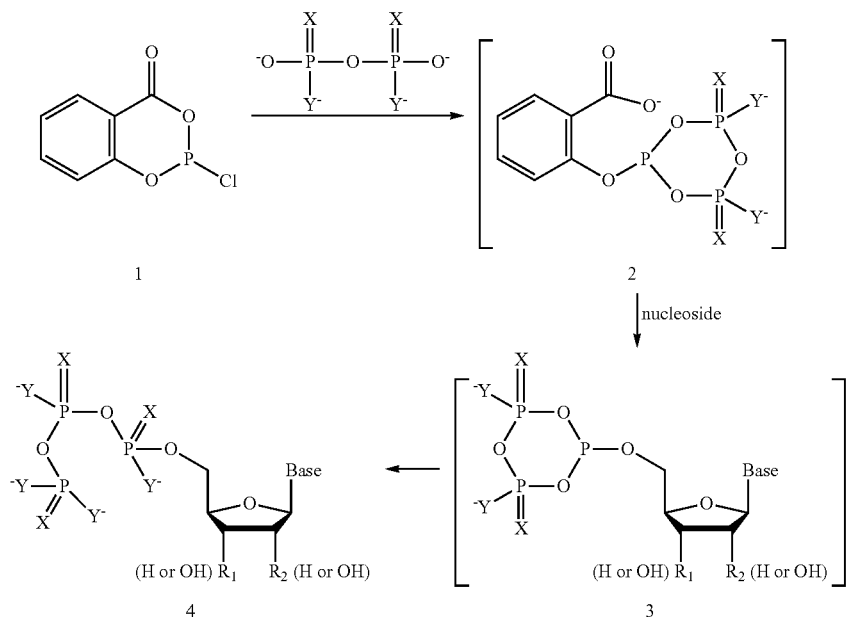

wherein in step (a), salicyl phosphorochloridite 1 or a derivative of said salicyl phosphorochloridite 1 is reacted temperature is from about room temperature to about 100° C.; and wherein in the conversion of said intermediate 3 to said product 4 of step (b), said suitable oxidative reagent is iodine and said suitable base is pyridine.

In some other forms, the disclosed processes are processes wherein said processes are carried out according to Scheme B,

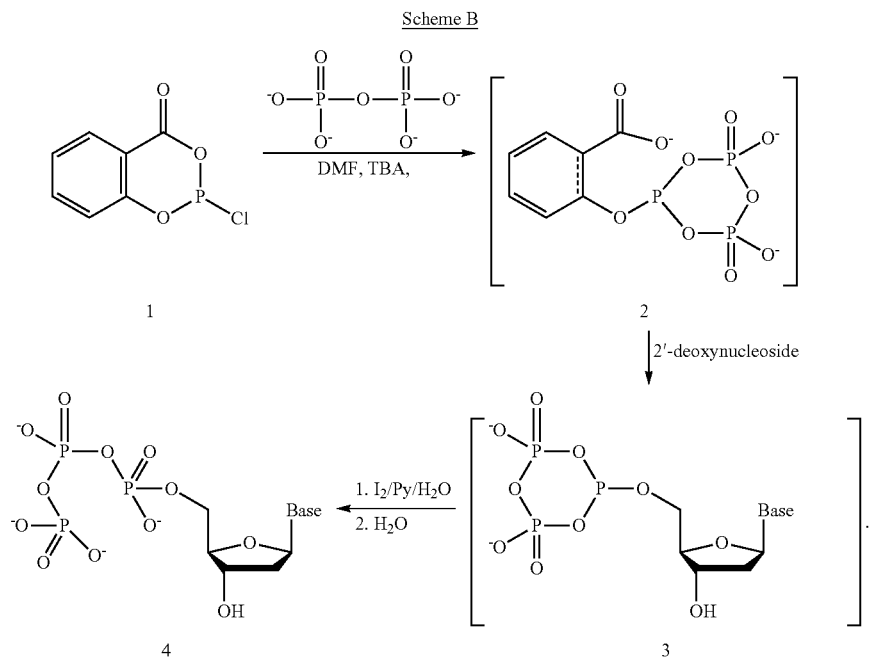

Scheme B

In some other forms, the disclosed processes are processes wherein said process is a one-pot reaction where no isolation or purification of said intermediates is needed and said product can be isolated or purified at the end of said process. In some other forms, the disclosed processes are processes wherein said process involves generation of an in situ, selective phosphorylating reagent (intermediate 2) that reacts selectively with the 5'-hydroxyl group of said nucleoside and subsequently forms said nucleoside 5'-triphosphate in one-pot. In some other forms, the disclosed processes are processes wherein said process does not involve protection and/or deprotection of amino and/or hydroxyl groups of said nucleoside.

In some other forms, the disclosed processes are processes wherein the formation of said intermediate 2 involves two nucleophilic displacement reactions: (i) a nucleophilic attack at the phosphorous center of said salicyl phosphorochloridite 1 exerted by the oxide group of the pyrophosphate displacing the chloride ion, and followed by (ii) a displacement of the carbonyl group upon a second attack of another oxide of pyrophosphate which provides the said intermediate 2. In some other forms, the disclosed processes are processes wherein the conversion of said intermediate 2 to said intermediate 3 is achieved where the 5'-hydroxyl group of said nucleoside exerts a nucleophilic attack on the phosphorous center of said intermediate 2, following ring opening of said intermediate 2 and subsequent displacement of the phenolic group during the intramolecular reaction to provide said intermediate 3.

In some other forms, the disclosed processes are processes wherein purified yield of said product from said process is from about 80% to about 100%. In some other forms, the disclosed processes are processes wherein said derivative is an oligonucleotide, DNA or RNA. In some other forms, the disclosed processes are processes wherein said nucleoside 5'-triphosphate can be incorporated into DNAs by DNA polymerase. In some other forms, the disclosed processes are processes wherein said nucleoside 5'-triphosphate is a substrate for DNA polymerase.

In some other forms, the disclosed processes are processes wherein said process can be applied to synthesize a base-modified nucleoside 5'-triphosphate. In some other forms, the disclosed processes are processes wherein said base-modified nucleoside 5'triphosphate has a base with a structure of formula (III),

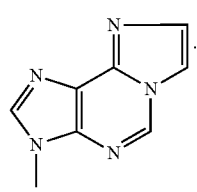

Formula (III)

The above disclosed processes do not require protection of either the base or sugar moiety of the nucleoside. The disclosed processes are more selectivity at the 5'-hydroxyl group than the 3' hydroxyl and time effective with comparable yields. The disclosed processes are examined by using all the four common 2'-deoxynucleosides: adenosine, cytosine, guanosine and thymidine and their use as substrates for the Klenow DNA polymerase.

A representative example of the above disclosed processes is illustarted in Scheme C (synthetic route for 2'-deoxynucleoside 5'-triphosphates as shown below). In the first step, the reaction of salicyl phosphorochloridite 1 with tributyl ammonium pyrophosphate provides the corresponding cyclic phosphite intermediate 2, (P2,P3-dioxo-P1-(salicyl)cyclotriphosphite). The formation of 2 can be monitored by $^{31}$P NMR after 30 min of the reaction which indicates a chemical shift of 98.9 ppm (see FIG. 1a). The formation of 2 could be as a result of two nucleophilic displacement reactions where at first, there is a nucleophilic attack at the phosphorous center of 1 exerted by the oxide group of the pyrophosphate displacing the chloride ion, followed by the displacement of the carboxylate group upon a second attack of another oxide of pyrophosphate affording the cyclic intermediate 2. The $^{31}$P NMR of salicyl phosphorochloridite carried out in DMF has a chemical shift of 124.6 ppm (singlet), whereas the $^{31}$P NMR of pyrophosphate is −10.0 ppm (see FIGS. 1c and d). The upfield shift from 124.6 ppm to 98.9 ppm (formation of an intermediate 2) is indicative of a change in the polarity of the group attached to the phosphorous atom.

The addition of intermediate 2 to the appropriate nucleosides brings about a $^{31}$P NMR chemical shift centered around 105 ppm (triplet) indicative of the formation of a phosphate group attached to 5'-oxygen of a nucleoside oxo-$P^1$-5'-(2'-deoxyribonucleosidyl-5'-O-) cyclotriphosphite 3. In the second step, the compound 3 is converted to the desired product 4 (2'-deoxynucleoside 5'-triphosphates) after oxidation with iodine and base hydrolysis. The disclosed processes of preparation are also used to synthesize a base-modified nucleoside 5'-triphosphate 4e. The disclosed processes of preparation are also applicable to the synthesis of alpha-modified nucleoside 5'-triphosphates. For instance, compound 3 may be oxidized with sulfur, selenium or a borane derivative to provide the corresponding nucleoside 5'-(α-P-thiotriphosphates) [J. Ludwig, F. Eckstein, *J. Org. Chem.* 1989, 54, 631-635], nucleoside 5'-(α-P-selenotriphosphates) [G. Brandt, N. Carrasco, Z. Huang, *Biochemistry* 2006, 45, 8972-7; N. Carrasco, J. Caton-Williams, G. Brandt, S. Wang, Z. Huang, *Angew Chem Int Ed Engl* 2005, 45, 94-7 10.1002/anie.200502215; N. Carrasco, J. Caton-Williams, G. Brandt, S. Wang, Z. Huang, *Angew Chem Int Ed Engl* 2006, 45, 94-7], or nucleoside 5'-(α-P-boranotriphosphates) [J. L. Lin, B. R. Shaw, *Chemical Communications* 2000, 2115-2116] respectively.

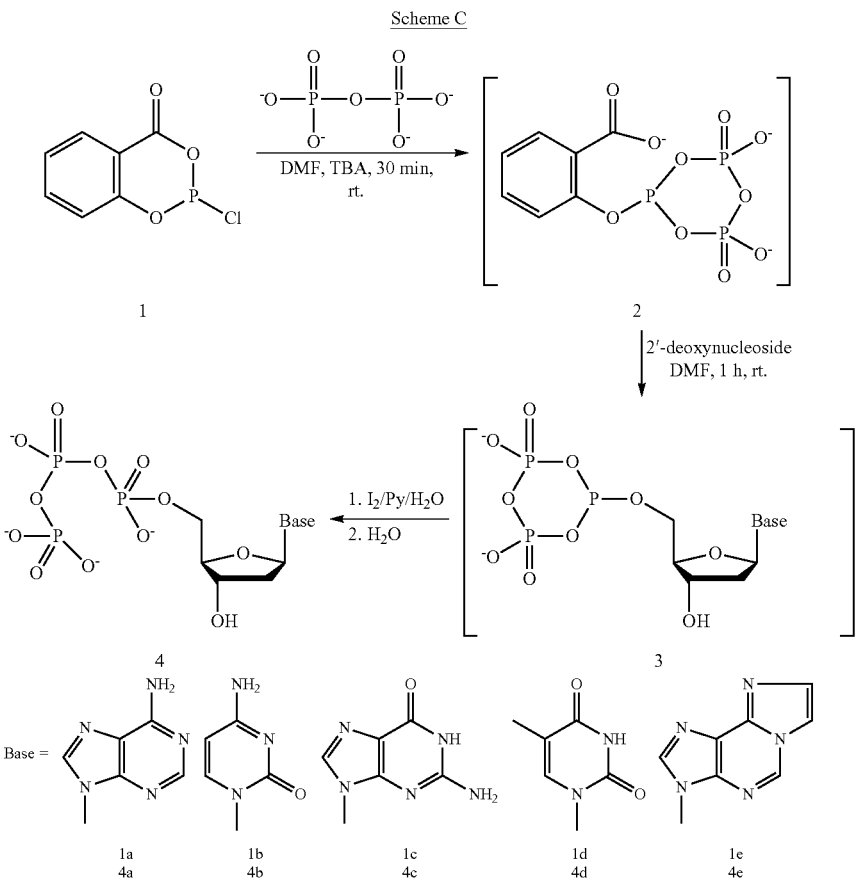

Scheme C which is in agreement with earlier studies conducted by others [J. Ludwig, F. Eckstein, *J. Org. Chem.* 1989, 54, 631-635; and B. K. Krzyzanowska, He, K. Hasan, A. Krzyzanowska, B. Shaw, *Tetrahedron* 1998, 54, 5119-5128]. The 5'-hydroxyl group of the nucleoside exerts a nucleophilic attack on the phosphorous center of the highly unstable intermediate 2, following ring opening of the cyclic intermediate and subsequent displacement of the phenolic group during the intramolecular reaction affording the $P^2$, $P^3$-di- Before any optimization of the above disclosed processes of preparation, the crude yields of the native 2'-deoxynucleoside 5'-triphosphate (e.g., nucleosides of dA, dC, dG or T) are at least greater than about 80%; and the HPLC yields of native 2'-deoxynucleoside 5'-triphosphate (e.g., nucleosides of dA, dC, dG or T) have a range from about 19% to about 46% after isolation (e.g., NaCl-ethanol isolation). With the optimization of the reaction conditions, the isolated yields have a range from about 80% to about 100%.

To reduce the effect of the undesired 3'-triphosphate, it is necessary to ensure that the starting reagents are completely consumed forming intermediate 2 prior to the addition of the nucleoside. No difficulty is encountered during the HPLC purification of the nucleoside triphosphates.

In some other forms, the disclosed processes are processes wherein said process can be applied to the synthesis of alpha-modified nucleoside 5'-triphosphate. In some other forms, the disclosed processes are processes wherein said alpha-modified nucleoside 5'-triphosphate is nucleoside 5'-(α-P-thiotriphosphates), nucleoside 5'-(α-P-selenotriphosphates), or nucleoside 5'-(α-P-boranotriphosphates). In some other forms, the disclosed processes are processes wherein said alpha-modified nucleoside 5'-triphosphate is synthesized via oxidation of said intermediate 3 by a suitable sulfur, selenium or borane reagent. In some other forms, the disclosed processes are processes wherein said suitable sulfur, selenium or borane reagent is 3H-benzo[d][1,2]thiaselenol-3-one.

In some other forms, the disclosed processes are processes wherein said alpha-modified nucleoside 5'-triphosphate is nucleoside 5'-(P-seleno)triphosphates (NTPαSe). In some other forms, the disclosed processes are processes wherein said nucleoside 5'-(P-seleno)triphosphates (NTPαSe) is synthesized according to Scheme D, in DMF (0.6 ml). The pyrophosphate and some TBA (1.2 ml) are injected into the bdpp. After 45 min, the uridine is dissolved in DMF (0.45 ml), and is then added to the ppi and bdpp. After stirring for 1 hr, the 3H-1,2-benzothaselenol-3-one (Btse), previously dissolved in dioxane (1.5 ml) is added to the mixture. The mixture is stirred for one hour and then hydrolyzed with water (10.2 ml, twice the volume). Two hours after hydrolysis and stirring, an ethanol precipitation is performed. The synthesized NTPαSes are then purified by reverse phase HPLC. NTPαSe is eluted using a combination of two solvents at varying proportions: buffer A (20 mM TEAAc in water) and buffer B (20 mM TEAAc, 50% water, 50% acetonitrile). Each diastereomer is collected independently. Fractions are lyophilized and one additional ethanol precipitation is performed for desalting.

Also disclosed are processes of preparation of all four nucleoside 5'-(P-seleno)triphosphates (NTPαSe), characterization of all four NTPαSe (A, C, G and U) and enzymatic incorporation of NTPαSe into a variety of RNA molecules using different types of templates for structure and function studies (See FIGS. 4-10). Except help phase determination on RNA X-ray crystallography, these NTPαSe offer new atomic mutations for illustration of the catalytic mechanism of functional RNAs and new chemical modifications options for RNA-related applications that require improvement on

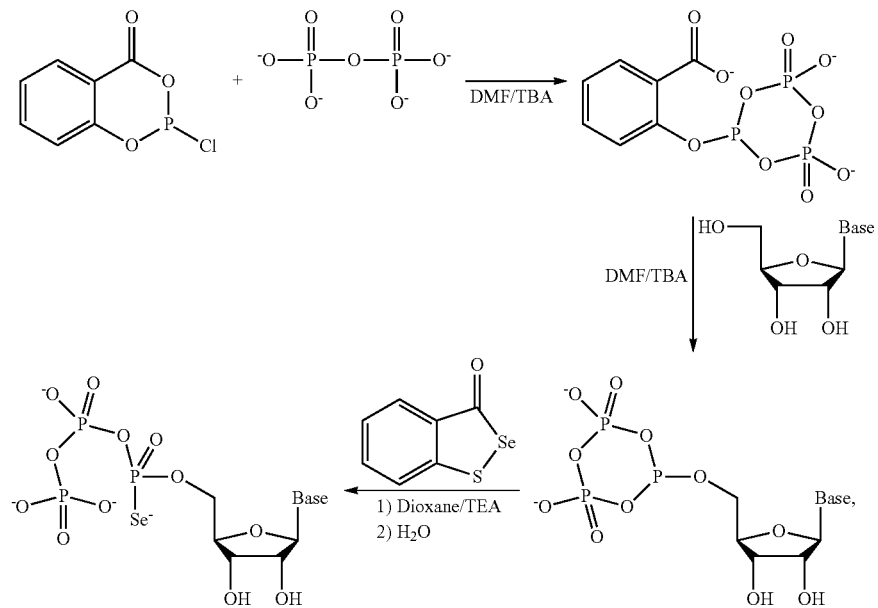

Scheme D (Synthesis of NTPαSe)

wherein the Base is Adenine (A), Cytosine (C), Guanine (G), Thymine (T), Uracil (U), modified nucleobase or unnatural nucleobase.

A representative procedure of Scheme D is performed under argon gas and all liquids are dried and purged with argon before use. Specifically, as a representative example of Scheme D, the nucleoside (109.8 mg, 0.45 mmol, 1 eq.), 3H-1,2-benzothaselenol-3-one (195 mg, 0.9 mmol, 2 eq.), tributylammonium pyrophosphate (426 mg, 0.9 mmol, 2 eq.) are dried in separate flasks in high vacuum for one hour. Then 2-chloro-4H-1,3,2-benzodioxaphosphorin-4-one (182 mg, 0.9 mmol, 1.5 eq.) is dried in a flask for 10 min. The tributylammonium pyrophosphate (ppi) and 2-chloro-4H-1,3,2-benzodioxaphosphorin-4-one (bdpp) are each dissolved performance, such as RNAi. Also disclosed are that the Se-derivatized DNAs grows crystals overnight with high-diffraction quality. Further disclosed are that the Se-derivatized DNA sequences crystallize under a broader range of buffer conditions, and generally have a faster crystal growth rate.

Definitions

A. A, an, the

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

B. Cell

The term "cell" as used herein also refers to individual cells, cell lines, or cultures derived from such cells. A "culture" refers to a composition comprising isolated cells of the same or a different type. The term co-culture is used to designate when more than one type of cell are cultured together in the same dish with either full or partial contact with each other.

C. Complex

The term complex as used herein refers to the association of a compound with an ion channel or enzyme for which the compound has a binding affinity.

D. Compound

For the purposes of the present disclosure the terms "compound," "analog," and "composition of matter" stand equally well for the chemical entities described herein, including all enantiomeric forms, diastereomeric forms, salts, and the like, and the terms "compound," "analog," and "composition of matter" are used interchangeably throughout the present specification.

E. Comprise

Throughout the description and claims of this specification, the word "comprise" and variations of the word, such as "comprising" and "comprises," means "including but not limited to," and is not intended to exclude, for example, other additives, components, integers or steps.

F. Components

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific form or combination of forms of the disclosed methods.

G. Control

The terms "control" or "control levels" or "control cells" are defined as the standard by which a change is measured, for example, the controls are not subjected to the experiment, but are instead subjected to a defined set of parameters, or the controls are based on pre- or post-treatment levels. They can either be run in parallel with or before or after a test run, or they can be a pre-determined standard.

H. Higher

The terms "higher," "increases," "elevates," or "elevation" or like terms or variants of these terms, refer to increases above basal levels, e.g., as compared a control. The terms "low," "lower," "reduces," "decreases" or "reduction" or variation of these terms, refer to decreases below basal levels, e.g., as compared to a control. For example, basal levels are normal in vivo levels prior to, or in the absence of, or addition of an agent such as an agonist or antagonist to activity. For example, decreases or increases can be used to describe the binding of a molecule to a receptor. In this context, decreases would describe a situation of where the binding could be defined as having a Kd of $10^{-9}$ M, if this interaction decreased, meaning the binding lessened, the Kd could decrease to $10^{-6}$ M. It is understood that wherever one of these words is used it is also disclosed that it could be 1%, 5%, 10%, 20%, 50%, 100%, 500%, or 1000% increased or decreased from a control.

I. Inhibit

By "inhibit" or other forms of inhibit means to hinder or restrain a particular characteristic. It is understood that this is typically in relation to some standard or expected value, in other words it is relative, but that it is not always necessary for the standard or relative value to be referred to. For example, "inhibits phosphorylation" means hindering or restraining the amount of phosphorylation that takes place relative to a standard or a control.

J. Maintaining

The word "maintaining" or like words refers to continuing a state. In the context of a treatment, maintaining can be refer to less than 20%, 15%, 10%, 9%, 8%, 7%, 6%, 5%, 4%, 3%, 2%, 1%, or 0.1% change from a control, such a basal level, often a level in the absence of a treatment or in the presence of treatment with a placebo or standard.

K. Material

Material is the tangible part of something (chemical, biochemical, biological, or mixed) that goes into the makeup of a physical object.

L. Modulate

The term modulate or like terms refers to its standard meaning of increasing or decreasing.

M. Substance

A substance or like terms is any physical object. A material is a substance. Molecules, ligands, markers, cells, proteins, DNA and RNA can be considered substances. A machine or an article would be considered to be made of substances, rather than considered a substance themselves.

N. Molecule

As used herein, the terms "molecule" or like terms refers to a biological or biochemical or chemical entity that exists in the form of a chemical molecule or molecule with a definite molecular weight. A molecule or like terms is a chemical, biochemical or biological molecule, regardless of its size.

Many molecules are of the type referred to as organic molecules (molecules containing carbon atoms, among others, connected by covalent bonds), although some molecules do not contain carbon (including simple molecular gases such as molecular oxygen and more complex molecules such as some sulfur-based polymers). The general term "molecule" includes numerous descriptive classes or groups of molecules, such as proteins, nucleic acids, carbohydrates, steroids, organic pharmaceuticals, small molecule, receptors, antibodies, and lipids. When appropriate, one or more of these more descriptive terms (many of which, such as "protein," themselves describe overlapping groups of molecules) will be used herein because of application of the method to a subgroup of molecules, without detracting from the intent to have such molecules be representative of both the general class "molecules" and the named subclass, such as proteins. Unless specifically indicated, the word "molecule" would include the specific molecule and salts thereof, such as pharmaceutically acceptable salts.

O. Optionally

"Optional" or "optionally" means that the subsequently described event or circumstance may or may not occur, and that the description includes instances where said event or circumstance occurs and instances where it does not.

P. Prevent

By "prevent" or other forms of prevent means to stop a particular characteristic or condition. Prevent does not require comparison to a control as it is typically more absolute than, for example, reduce or inhibit. As used herein, something could be reduced but not inhibited or prevented, but something that is reduced could also be inhibited or prevented. Similarly, something could be reduced and inhibited, but not prevented. It is understood that where reduce, inhibit or prevent are used, unless specifically indicated otherwise, the use of the other two words is also expressly disclosed. Thus, if inhibits phosphorylation is disclosed, then reduces and prevents phosphorylation are also disclosed.

Q. Ranges

Ranges can be expressed herein as from "about" one particular value, and/or to "about" another particular value. When such a range is expressed, some forms includes from the one particular value and/or to the other particular value. Similarly, when values are expressed as approximations, by use of the antecedent "about," it will be understood that the particular value forms some forms. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data are provided in a number of different formats, and that this data, represents endpoints and starting points, and ranges for any combination of the data points. For example, if a particular datum point "10" and a particular datum point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

R. Reduce

By "reduce" or other forms of reduce means lowering of an event or characteristic. It is understood that this is typically in relation to some standard or expected value, in other words it is relative, but that it is not always necessary for the standard or relative value to be referred to. For example, "reduces phosphorylation" means lowering the amount of phosphorylation that takes place relative to a standard or a control.

S. References

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

T. Specifically interacts

Specifically interacts or like terms means that the interaction is beyond a background interaction. The background interaction can be determined by for example looking at the interaction with serum albumin.

U. Subject

As used throughout, by a "subject" is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human. The subject can also be a non-human.

V. Tissue

Tissue or like terms refers to a collection of cells. Typically a tissue is obtained from a subject.

W. TBA

As used herein, the acronym "TBA" means tributylamine.

X. TEA

As used herein, the acronym "TEA" means triethylammonium.

Y. EdATP

As used herein, the term "EdATP" means $1,N^6$ ethenoadenosine triphosphate.

Z. DMF

As used herein, the term "DMF" means dimethylformamide.

EXAMPLES

The following examples are put forth so as to provide those of ordinary skill in the art with a complete disclosure and description of how the compounds, compositions, articles, devices, systems and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Figure 2:
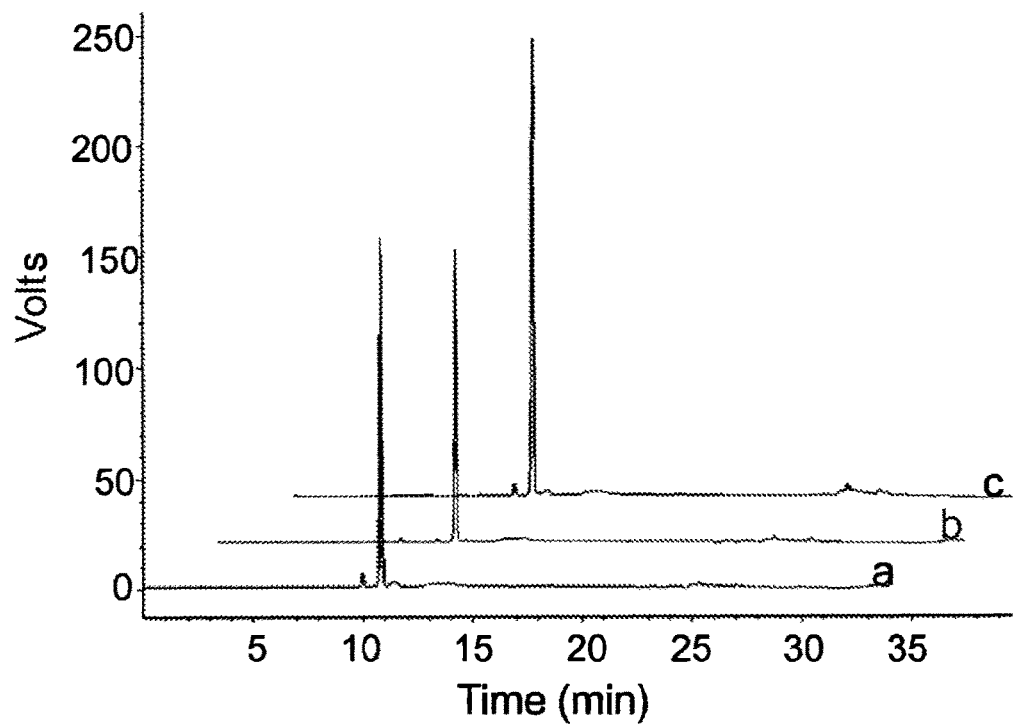
FIG. 2 shows a typical HPLC profile of chemically synthesized and commercially available 2'-deoxynucleoside 5'-triphosphate. After a NaCl-ethanol precipitation, samples were analyzed on a Welsch C18 reversed phase analytical column (4.6×250 mm) measured at 260 nm at a flow of 1.0 mL/min and with a linear gradient of 0 to 25% B in 20 min. Buffer A: mM triethylammonium acetate (TEAAc, pH 7.1) and buffer B: 50% acetonitrile in 10 mM TEAAc (pH 7.1). a) Test dCTP (injected 7.5 µL, 1.0 mM, retention time 10.78 min). b) Standard dCTP (injected 7.5 µL, 1.0 mM, retention time 10.77 min). c) Co-injection (injected 15 µL 1.0 mM, retention time 10.89 min).

A. Example No. 1: Determination of the Formation of 5'-triphosphate Rather than the 3'-triphosphate Counterpart To determine whether the 5'-triphosphate is formed and not the 3'-triphosphate counterpart owing to the lack of a 3'-protection, HPLC analysis of the synthesized 5'-triphosphate was compared with the commercially available nucleosides 5'-triphosphate (dATP, dCTP, dGTP, TTP) used as standards (see FIG. 2). The dNTP standards were used for establishing an HPLC working curve from which the yields were calculated. The standards were then injected under the same HPLC conditions as the chemically synthesized (test) triphosphates and their retention times noted. In addition, co-injections of the corresponding standards and the isolated triphosphates (test) were performed. A typical HPLC profile is illustrated in FIG. 2. From the HPLC profiles, it was observed that the retention times for both the standards and the corresponding chemically synthesized triphosphate were similar. A single peak resulting from each co-injection confirmed that indeed the 5'-triphosphates isolated were similar to the corresponding standards, and clearly, the 3'-counterpart was not present. Furthermore, all the dNTPs synthesized were confirmed by NMR ($^1$H and $^{31}$P) and mass spectroscopy analyses (see Table 1). The similarity of the mass-charge ratios confirms that the triphosphates synthesized have molecular formula similar to the corresponding commercially available 5'-dNTPs.

TABLE 1

ESI-TOF [M − H]$^-$ mass spectrometry analysis of 2'-deoxynucleoside 5'-triphosphates

| Entry | 5'-Triphosphate | Chemical Formula | Measured | (Calcd.) m/z |
|---|---|---|---|---|
| 4a | dATP | $C_{10}H_{16}N_5O_{12}P_3$ | 489.9938 | (489.9936) |
| 4b | dCTP | $C_9H_{16}N_3O_{13}P_3$ | 465.9814 | (465.9817) |
| 4c | dGTP | $C_{10}H_{16}N_5O_{13}P_3$ | 505.9893 | (505.9885) |
| 4d | TTP | $C_{10}H_{17}N_2O_{14}P_3$ | 480.9831 | (480.9820) |
| 4e | EdATP | $C_{12}H_{15}N_5O_{12}P_3$ | 513.9940 | (513.9936) |

Figure 3:
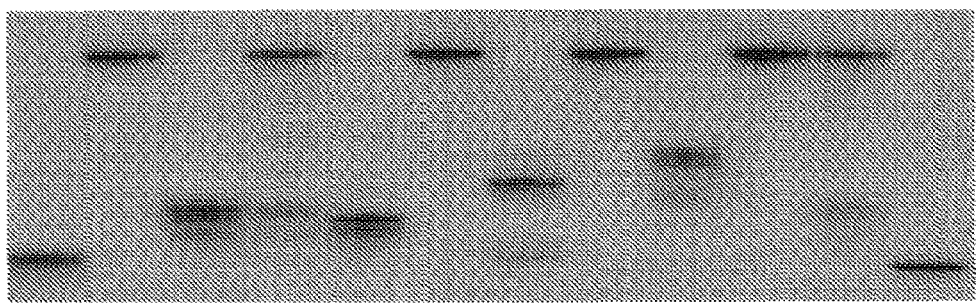
FIG. 3A shows Primer and template sequences used in the polymerization experiment.
FIG. 3B shows Primer extension reaction of chemically synthesized dNTPs and commercially available dNTPs into DNA by Klenow fragment exo(−), Kf-. Primer, P was end labeled using polynucleotide kinase and [γ-$^{32}$P] ATP. Polymerization reactions were performed with 3.5 µM primer and 5 µM template and equimolar ratios of all dNTPs (0.1 mM) and incubated with 0.05 of DNA polymerase per µL at 37° C. for 1 h. Reaction was analyzed by 19% polyacrylamide gel electrophoresis. Lane 1: primer, P and all dNTPs but no Kf-; lane 2: P plus template, T and all dNTPs (Epicentre, Inc.) with Kf-; lane 3: P/T and all dNTPs except dATP with Kf-; lane 4: P/T and test dATP, dCTP, dGTP, and TTP with Kf-; lane 5: P/T and all dNTPs except dCTP with Kf-; lane 6: P/T and dATP, test dCTP, dGTP and TTP with Kf-; lane 7: P/T and all dNTPs except dGTP with Kf-; lane 8: P/T and dATP, dCTP, test dGTP and TTP with Kf-; lane 9: P/T and all dNTPs except TTP with Kf-; lane 10: P/T and dATP, dCTP, dGTP and test TTP with Kf-; lane 11: P/T and all test dNTPs with Kf-; lane 12: primer, P.
Figure 4A:
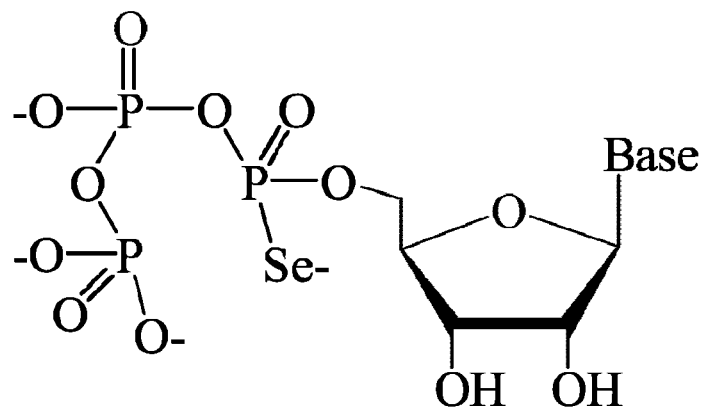
FIG. 4A shows NTPαSe structure and FIG. 4B shows structure of Rp phosphoroselenoate RNA.
Figure 4B:
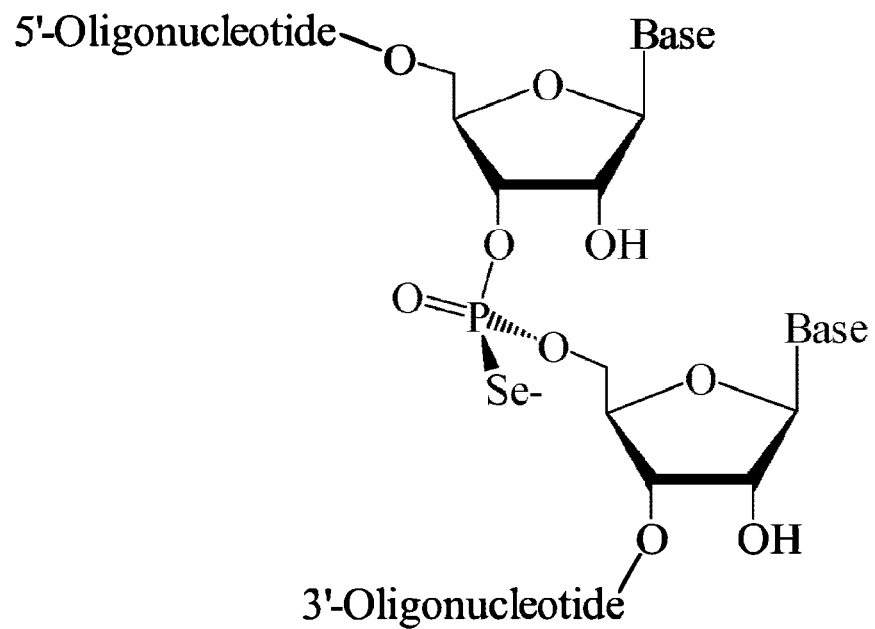
Figure 5:
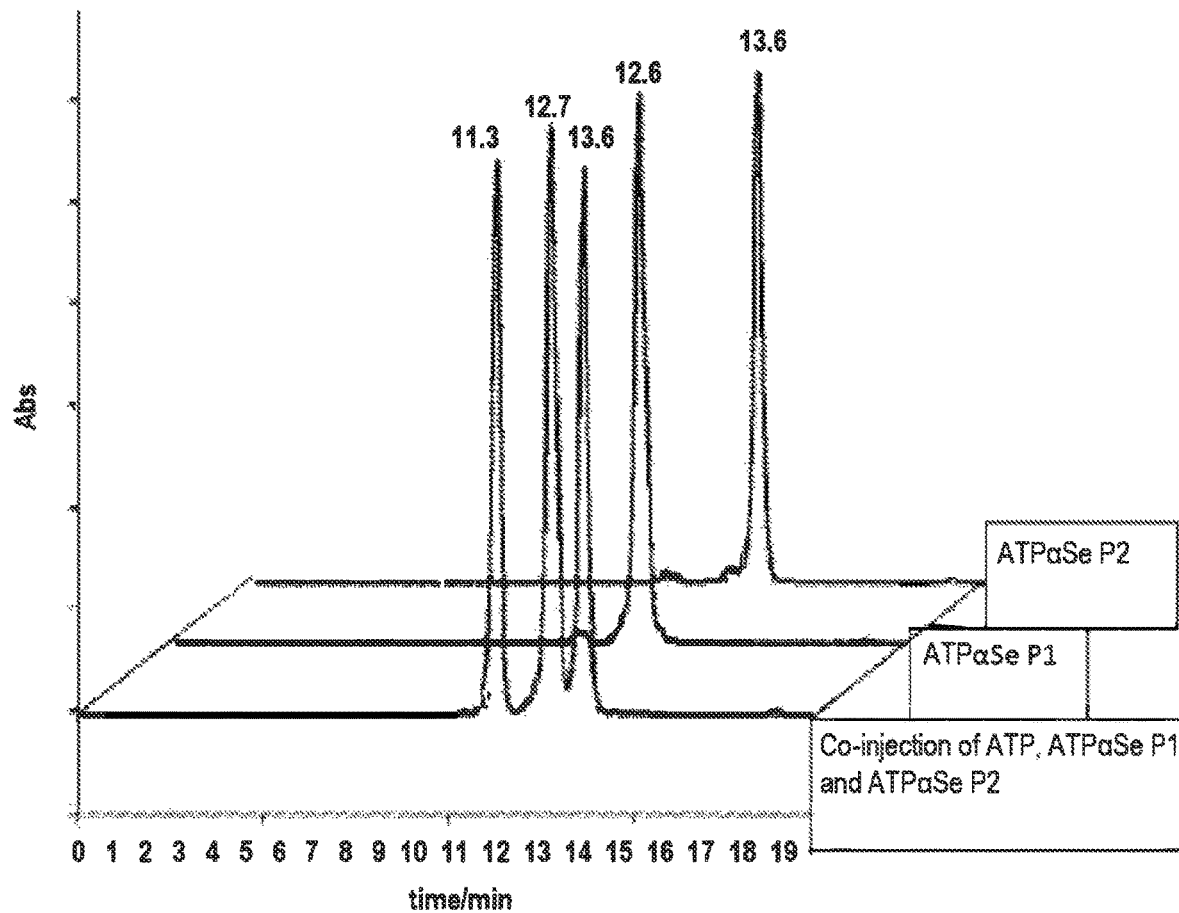
FIG. 5 shows HPLC profiles of ATP, ATPαSe diastereomers P1 and P2. 20 min 25% acetonitrile.
Figure 6:
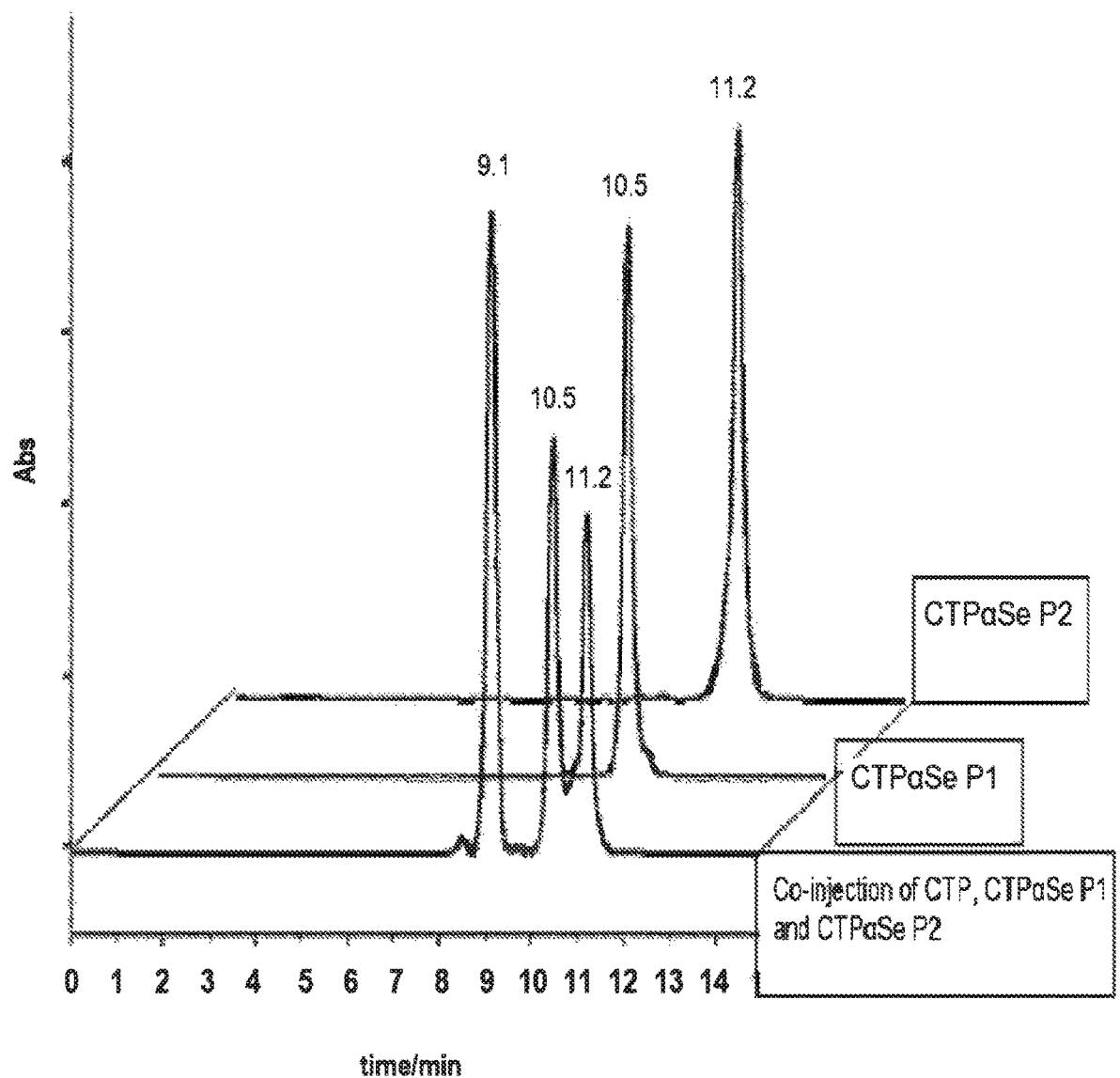
FIG. 6 shows HPLC profiles of CTP, CTPαSe diastereomers P1 and P2. 20 min 25% acetonitrile.
Figure 7:
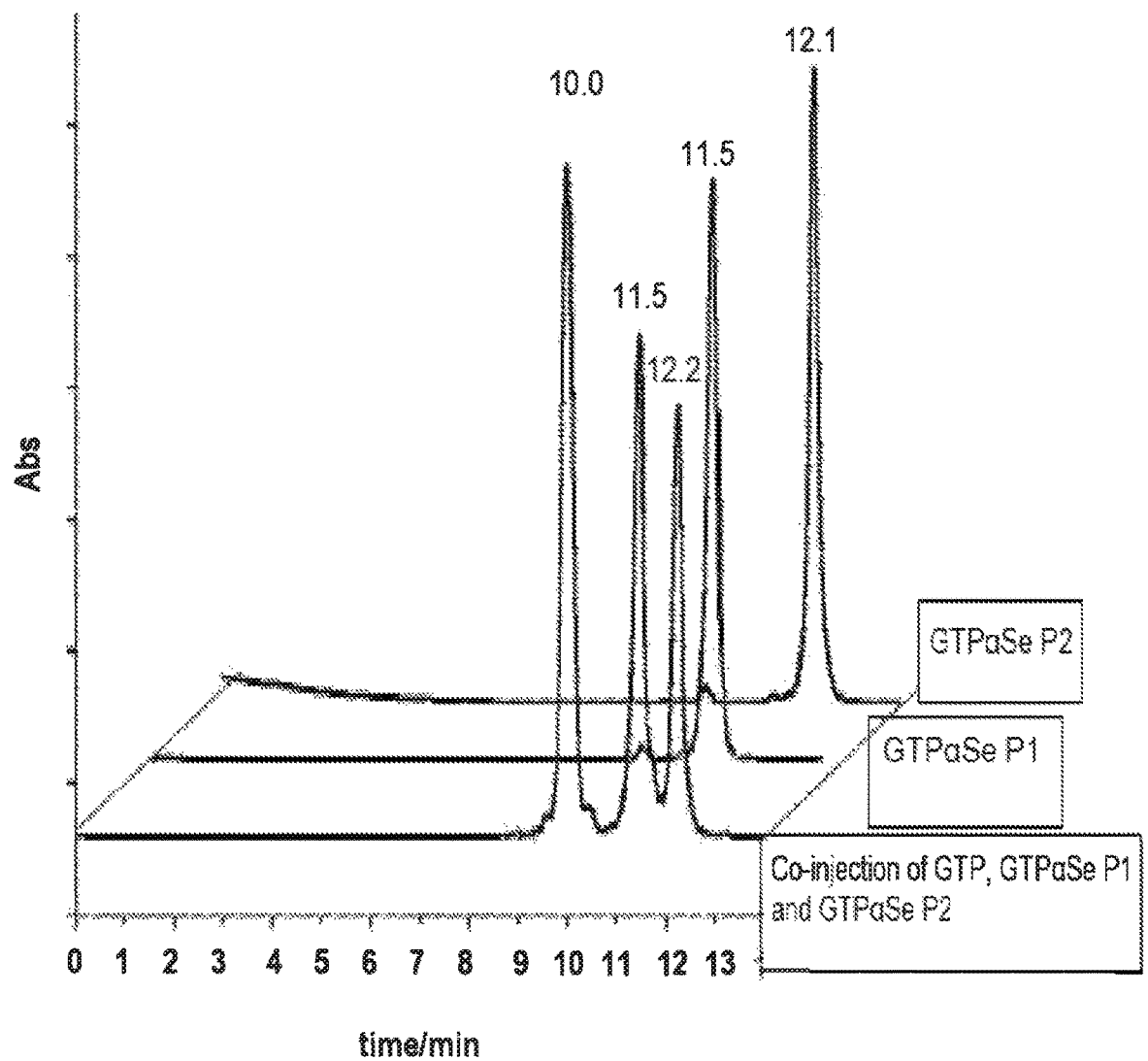
FIG. 7 shows HPLC profiles of GTP, GTPαSe diastereomers P1 and P2. 20 min 25% acetonitrile.
Figure 8:
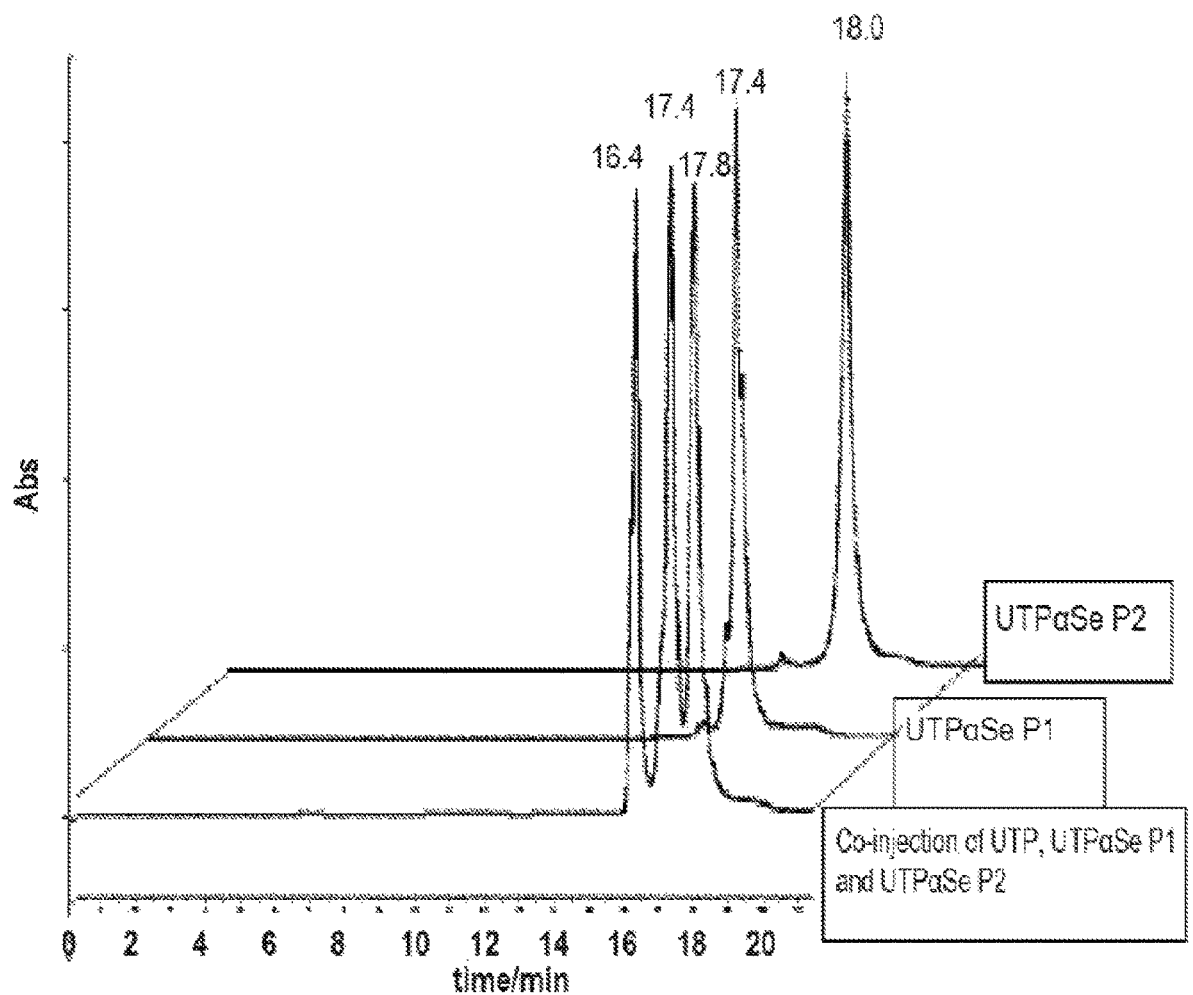
FIG. 8 shows HPLC profiles of UTP, UTPαSe diastereomers P1 and P2. 20 min 40% Ethanol.
Figure 9:
FIG. 9 shows enzymatic incorporation of NTPαSe diastereomers P1 and P2 to Hammerhead ribozyme RNA using plasmid template.
Figure 10:
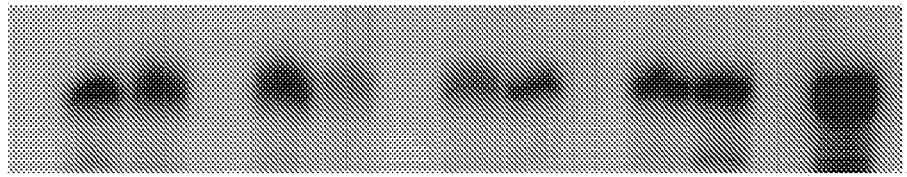
FIG. 10 shows enzymatic incorporation of NTPαSe diastereomers P1 and P2 to Hammerhead ribozyme55.27 using synthetic templates.

B. Example No. 2: Further Determination of the Formation of the Nucleoside 5'-triphosphates To further demonstrate that the nucleoside 5'-triphosphates were indeed synthesized, their ability to serve as substrates for the Klenow polymerase were explored. For the polymerase extension reaction, the primer (SEQ ID NO: 1; P: 5'-d-GCG TAA TAC GAC TCA CTA TAG-3') was radiolabeled with [γ-$^{32}$P] ATP at the 5'-position and incubated with the template (SEQ ID NO: 2; 3'-d-GCAT-TATGCTGAGTGATATCGTCTGGAC-TACTCCGGCTTTCCGGCTTTGCATGT-5') to allow examination of a test nucleotide (dATP, dCTP, dGTP or TTP), see FIG. 3. The polymerase reaction was conducted in the presence of the Klenow polymerase (0.05 U/μL). In FIG. 3, it was observed that the polymerase efficiently extended the primer for each reaction containing a single test dNTP (lanes: 4, 6, 8 and 10) to the expected full-length as the standard triphosphates (lane 2). As expected, polymerization reactions in the absence of one dNTP (lanes: 3, 5, 7 and 9) did not show full-length product. More convincingly, in a reaction containing each of the test triphosphates (lane 11), full-length product (SEQ ID NO: 3) similar to the standard polymerization reaction (lane 2) was observed.

C. Example No. 3: Enzymatic Incorporation of NTPαSe and Purification of Phosphoroselenoate Modified RNA (P-Se-RNA)

In a representative example of the present disclosure, 500 μL mutant hammerhead ribozyme transcripts were prepared according to the manual of the manufacturer (Epicentre T7 flash transcription kit) with extra 0.1 u/μ phosphatase and 2 mM MnCl$_2$ in reaction buffer for 2 h. 100 mM UTPαSe was used to substitute normal 100 mM UTP from the kit. The transcription result was checked by 12% denaturing PAGE gel using UV shadowing. After transcription, 10 μL (10 u) Dnase I was added at 37° C. for 15 min to remove DNA template. Ethanol precipitation was performed to remove part of short RNA and NTP. The pellet was redissolved in 100 μL water. Se-P-U hammerhead ribozyme transcript was further purified by 12% denaturing PAGE. RNA was recovered from the gel soaking solution. Ethanol precipitation was then performed to pellet RNA from solution. The redissolved hammerhead ribozyme was desalted by 10K centrifugal membrane filter (Pall). 55.27 RNA sequence: SEQ ID NO: 4; 5 '-GGC AAC CUG AUG AGG CCG AAA GGC CGA AAC G UACA-3 55.27 DNA templates: SEQ ID NO: 5; 3'-CGCATTATGCTGAGTGATATCCGTTGGAC-TACTCCGGCTTTCCGGCTTTGCA TGT-5'. Wild type hammerhead ribozyme RNA: SEQ ID NO: 6; 5 '-GG-GAGCCCUGUCACCGGAUGUGCUUUCCGGU-CUGAUGAGUCCGUGAGGACGAA ACAGGG-CUCCCGAAUU-3'. Wild type hammerhead ribozyme template: SEQ ID NO: 7; 3'-CGCATTATGCTGAGTGA-TATCCCTCGGGACAGTGGCCTACACGAAAGGCCA-GAC TACTCAGGCACTCCTGCTTTGTCCCGAGGGCT-TAA-5'.

D. Example No. 4: MS and NMR Data for Representative NTPαSe Synthesized According to the Present Disclosure UTPαSe P1 molecular formular $C_9H_{15}N_2O_{14}P_3$Se, observed [M]$^-$=546.8848 (calcd. 546.8901). UTPαSe P2 molecular formular $C_9H_{15}N_2O_{14}P_3$Se, observed [M]$^-$=546.8818 (calcd. 546.8901). CTPαSe P1 molecular formular $C_9H_{16}N_3O_{13}P_3$Se, observed [M]$^-$=545.8989 (calcd. 545.8983). CTPαSe P2 molecular formular $C_9H_{16}N_3O_{13}P_3$Se, observed [M]$^-$=545.8972 (calcd. 545.8983). ATPαSe P1 molecular formular $C_{10}H_{16}N_5O_{12}P_3$Se, observed [M]$^-$=569.9082 (calcd. 569.9174). ATPαSe P2 molecular formular $C_{10}H_{16}N_5O_{12}P_3$Se, observed [M]$^-$=569.9077 (calcd. 569.9174). GTPαSe P1 molecular formular $C_{10}H_{16}N_5O_{13}P_3$Se, observed [M]$^-$=585.9043 (calcd. 585.9044). GTPαSe P2 molecular formular $C_{10}H_{16}N_5O_{13}P_3$Se, observed [M]$^-$=585.9052 (calcd. 585.9044).

UTPαSe P1: $^1$H NMR (400 MHz, D$_2$O), δ 3.57-3.67 (m, 2H, H5'), 4.20-4.41 (m, 3H, H4'+H3'+H2'), 5.91 (d, 1H, H5), 5.93 (d, 1H, H1'), 8.54 (d, 1H, H6); $^{13}$C NMR (100 MHz, D$_2$O), δ 64.64 (C-5'), 69.63 (C-2'), 73.69 (C-3'), 83.10 (C-1'), 88.13 (C-4'), 102.70 (C-5), 142.13 (C-6), 151.92 (C-2), 166.31 (C-4); $^{31}$P NMR (161.97 MHz, D$_2$O) δ 32.82 (d, J$_{α,β}$=29.96 Hz, αP), −6.50 (d, J$_{β,γ}$=19.40 Hz, γP), −23.21 (dd, J=21.06 Hz, βP).

UTPαSe P2: $^1$H NMR (400 MHz, D$_2$O), δ 3.58 (m, 2H, H5'), 4.23-4.53 (m, 3H, H4'+H3'+H2'), 5.92 (t, 1H, H5), 6.12 (d, 1H, H1'), 8.03 (d, 1H, H6); $^{13}$C NMR (100 MHz, D$_2$O), δ 65.46 (C-5'), 69.58 (C-2'), 73.75 (C-3'), 83.21 (C-1'), 88.15 (C-4'), 102.77 (C-5), 142.98 (C-6), 151.92 (C-2), 166.33 (C-4); $^{31}$P NMR (161.97 MHz, D$_2$O) δ 33.68 (d, J$_{α,β}$=34.02 Hz, αP), −5.63 (d, J$_{β,γ}$=19.44 Hz, γP), −22.48 (dd, J=18.36 Hz, βP).

CTPαSe P1: $^1$H NMR (400 MHz, D$_2$O), δ 3.58 (m, 2H, H5'), 4.22-4.38 (m, 3H, H4'+H3'+H2'), 5.93 (d, 1H, H1'), 6.11 (d, 1'-1, H5), 8.05 (d, 1H, H6); $^{13}$C NMR (100 MHz, D$_2$O), δ 64.43 (C-5'), 69.40 (C-2'), 74.20 (C-3'), 82.51 (C-1'), 89.02 (C-4'), 96.78 (C-5), 142.03 (C-6), 157.80 (C-2), 166.17 (C-4); $^{31}$P NMR (161.97 MHz, D$_2$O) δ 33.59 (d, J$_{α,β}$=34.01 Hz, αP), −9.14 (d, J$_{β,γ}$=19.44 Hz, γP), −23.97 (dd, J=17.28 Hz, βP).

CTPαSe P2: $^1$H NMR (400 MHz, D$_2$O), δ 3.58 (m, 2H, H5'), 4.23-4.37 (m, 3H, H4'+H3'+H2')), 5.93 (d, 1H, H1'), 6.11 (d, 1H, H5), 7.97 (d, 1H, H6); $^{13}$C NMR (100 MHz, D$_2$O), δ 65.13 (C-5'), 69.30 (C-2'), 73.90 (C-3'), 82.53 (C-1'), 88.92 (C-4'), 96.63 (C-5), 141.77 (C-6), 157.80 (C-2), 165.2 (C-4); $^{31}$P NMR (161.97 MHz, D$_2$O) δ 33.17 (d, J$_{α,β}$=30.77 Hz, αP), −7.11 (d, J$_{β,γ}$=19.44 Hz, γP), −23.39 (dd, J=17.82 Hz, βP).

ATPαSe P1: $^1$H NMR (400 MHz, D$_2$O), δ 3.66 (m, 2H, H5'), 4.19-4.56 (m, 3H, H4'+H3'+H2')), 6.06 (d, 1H, H1'), 8.17 (s, 1H, H2), 8.84 (s, 1H, H8); $^{13}$C NMR (100 MHz, D$_2$O), δ 64.88 (C-5'), 70.51 (C-2'), 74.26 (C-3'), 83.77 (C-1'), 86.79 (C-4'), 118.59 (C-5), 140.39 (C-8), 149.17 (C-4), 152.80 (C-2), 155.61 (C-6); $^{31}$P NMR (161.97 MHz, D$_2$O) δ 34.04 (d, J$_{\alpha,\beta}$=32.34 Hz, αP), −6.89 (d, J$_{\beta,\gamma}$=19.44 Hz, γP), −22.77 (dd, J=17.28 Hz, βP).

ATPαSe P2: $^1$NMR (400 MHz, D$_2$O), δ 3.58 ((m, 2H, H5'), 4.15-4.57 (m, 3H, H4'+H3'+H2')), 6.06 (d, 1H, H1'), 8.16 (s, 1H, H2), 8.55 (s, 1H, H8); $^{13}$C NMR (100 MHz, D$_2$O), δ 65.75 (C-5'), 70.32 (C-2'), 74.30 (C-3'), 83.75 (C-1'), 86.82 (C-4'), 118.50 (C-5), 140.14 (C-8), 149.07 (C-4), 152.75 (C-2), 155.51 (C-6); $^{31}$P NMR (161.97 MHz, D$_2$O) δ 33.82 (d, J$_{\alpha,\beta}$=34.01 Hz, αP), −6.16 (d, J$_{\beta,\gamma}$=19.44 Hz, γP), −22.65 (dd, J=18.36 Hz, βP).

GTPαSe P1: $^1$NMR (400 MHz, D$_2$O), δ 3.58 (m, 2H, H5'), 4.18-4.56 (m, 3H, H4'+H3'+H2')), 5.85 (d, 1H, H1'), 8.12 (s, 1H, H8); $^{13}$C NMR (100 MHz, D$_2$O), δ 65.36 (C-5'), 70.67 (C-2'), 73.63 (C-3'), 83.72 (C-1'), 86.63 (C-4'), 116.10 (C-5), 138.03 (C-8), 151.84 (C-4), 153.92 (C-2), 158.86 (C-6); $^{31}$P NMR (161.97 MHz, D$_2$O) δ 33.77 (d, J$_{\alpha,\beta}$=32.39 Hz, αP), −9.54 (d, J$_{\beta,\gamma}$=19.44 Hz, γP), −23.96 (dd, J=17.28 Hz, βP).

GTPαSe P2: $^1$H NMR (400 MHz, D$_2$O), δ 3.65 (m, 2H, H5'), 4.18-4.52 (m, 3H, H4'+H3'+H2')), 5.85 (d, 1H, H1'), 8.19 (s, 1H, H8); $^{13}$C NMR (100 MHz, D$_2$O), δ 65.77 (C-5'), 70.55 (C-2'), 73.76 (C-3'), 83.68 (C-1'), 86.63 (C-4'), 115.83 (C-5), 137.68 (C-8), 151.71 (C-4), 153.89 (C-2), 158.69 (C-6); $^{31}$P NMR (161.97 MHz, D$_2$O) δ 33.09 (d, J$_{\alpha,\beta}$=32.39 Hz, αP), −6.26 (d, J$_{\beta,\gamma}$=21.06 Hz, γP), −23.12 (dd, J=17.82 Hz, βP).

Discussion and Summary

Because nucleosides comprise amino and multi-hydroxyl groups, the synthesis of the nucleoside 5'-triphosphates requires protection and deprotection of these groups, which are achieved in multiple synthetic steps. In order to simplify the triphosphate synthesis and avoid the protection and deprotection reactions, disclosed are novel and convenient processes of preparation of nucleoside 5'-triphosphates (i.e., 2'-deoxynucleoside 5'-triphosphates (dNTPs)) without nucleoside protection. The facile synthesis is achieved by generating an in situ, selective phosphorylating reagent that reacts selectively with the 5'-hydroxyl group and finally generates the triphosphates in one-pot. The synthesized triphosphates are of high quality and can be effectively incorporated into DNAs by DNA polymerase. The disclosed processes of preparation are mild and are also useful in one-pot synthesis of modified triphosphates. In short, the synthesis of all the naturally occurring nucleoside 5'-triphosphates (i.e., 2'-deoxynucleoside 5'-triphosphates) via a phosphite intermediate 2 in the absence of protecting groups has been accomplished. The idea to first react the 2-chloro-4-H-1,3,2-benzodioxaphosphorin-4-one (salicyl phosphorochloridite) and tributyl ammonium pyrophosphate together to form the phosphite intermediate 2 serves as a good selective reagent to generate high selectivity at the 5'-hydroxyl position over the 3'-hydroxyl position of an unprotected nucleoside. These processes of preparation open the possibility of preparing triphosphates that would be compatible to the mild synthetic conditions. Indeed, all the synthesized dNTPs accordingly to the presently disclosed processes are substrates for Klenow polymerase and all are incorporated to give full length products.

REFERENCES

G. Storz, *Science* 2002, 296, 1260-3.
M. T. McManus, P. A. Sharp, *Nat Rev Genet.* 2002, 3, 737-47.
M. Mandal, R. R. Breaker, *Nat Rev Mol Cell Biol* 2004, 5, 451-63.
G. Gish, F. Eckstein, *Science* 1988, 240, 1520-2.
F. Eckstein, *Annu Rev Biochem* 1985, 54, 367-402 10.1146/annurev.bi.54.070185.002055.
N. A. Golubeva, Ivanov, A. V., vanov, M. A., Batyunina, O. A., Shipitsyn, A. V. Tunitskaya, V. L. and Alexandrova, L. A., *Mosco UniversityChemistry Bulletin* 2008, 63, 89-93.
A. M. Maxam, W. Gilbert, *Proc Natl Acad Sci USA* 1977, 74, 560-4.
G. Elia, C. Belloli, F. Cirone, M. S. Lucente, M. Caruso, V. Martella, N. Decaro, C. Buonavoglia, P. Ormas, *Antiviral Res* 2008, 77, 108-13.
E. M. August, M. E. Marongiu, T. S. Lin, W. H. Prusoff, *Biochem Pharmacal* 1988, 37, 4419-22.
H. Mitsuya, R. Yarchoan, S. Broder, *Science* 1990, 249, 1533-44.
K. Lohmann, *Naturwiss* 1929, 17, 624-625.
C. H. Fiske, Y. Subbarow, *Science* 1929, 70, 381-382.
K. Lohmann, *Biochem. Z.* 1931, 233, 460-466.
T. Satoh, *J. Biochem. Jpn.* 1935, 2, 19-36.
C. L. Harvey, E. M. Clericuzio, A. L. Nussbaum, *Anal Biochem* 1970, 36, 413-21.
m. Asada, nakanishi, k., agric. *Biol. Chem.* 1978, 42, 1533-1538.
T. F. Walseth, R. A. Johnson, *Biochim Biophys Acta* 1979, 562, 11-31.
J. Baddiley, Michelson, A. M. and Todd, A. R., *J. Chem. Soc. London* 1949, 582-586.
J. Ludwig, F. Eckstein, *J. Org. Chem.* 1989, 54, 631-635.
K. Burgess, D. Cook, *Chem Rev* 2000, 100, 2047-60.
Y. Ahmadibeni, R. K. Tiwari, G. Sun, K. Parang, *Org Lett* 2009, 11, 2157-60 10.1021/ol900320r.
W. Wu, C. L. Freel Meyers, R. F. Borch, *Org Lett* 2004, 6, 2257-60 10.1021/ol049267j.
Q. Sun, J. P. Edathil, R. Wu, E. D. Smidansky, C. E. Cameron, B. R. Peterson, *Org Lett* 2008, 10, 1703-6 10.1021/ol8003029.
S. Warnecke, C. Meier, Nucleic Acids Symp Ser (Oxf) 2008, 583-4 nrn295 [pii] 10.1093/nass/nrn295.
A. T. Horhota, J. W. Szostak, L. W. McLaughlin, *Org Lett* 2006, 8, 5345-7 10.1021%1062232u.
M. Yoshikawa, T. Kato, T. Takenishi, *Tetrahedron Lett* 1967, 50, 5065-8.
S. Aketani, K. Tanaka, K. Yamamoto, A. Ishihama, H. Cao, A. Tengeiji, S. Hiraoka, M. Shiro, M. Shionoya, *J Med Chem* 2002, 45, 5594-603 jm020193w [pii].
R. S. J. H. R. J. H. S. J. H. Beijnen, *Nucleosides, Nucleotides and Nucleic Acids* 2009, 29, 14-26.
W. Wu, D. E. Bergstrom, V. J. Davisson, *J Org Chem* 2003, 68, 3860-5 10.1021/jo020745i.
B. K. Krzyzanowska, He, K. Hasan, A. Krzyzanowska, B. Shaw, B. R., *Tetrahedron* 1998, 54, 5119-5128.
G. Brandt, N. Carrasco, Z. Huang, *Biochemistry* 2006, 45, 8972-7.
N. Carrasco, J. Caton-Williams, G. Brandt, S. Wang, Z. Huang, *Angew Chem Int Ed Engl* 2005, 45, 94-7 10.1002/anie.200502215.
N. Carrasco, J. Caton-Williams, G. Brandt, S. Wang, Z. Huang, *Angew Chem Int Ed Engl* 2006, 45, 94-7.
J. L. Lin, B. R. Shaw, *Chemical Communications* 2000, 2115-2116.

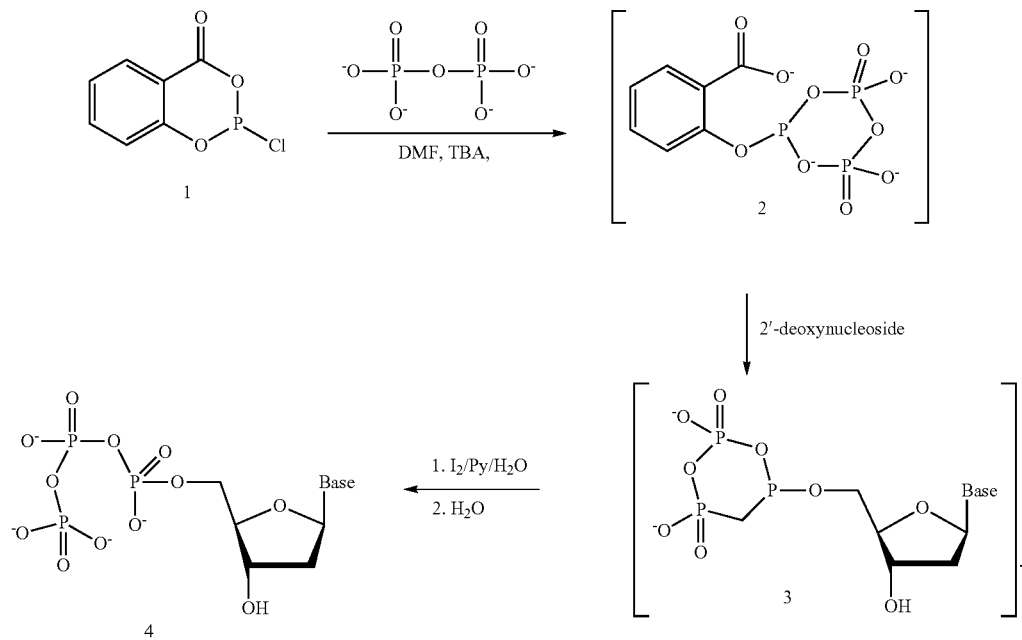

What is claimed is:

1. A process of preparing a nucleoside 5'-α-P-selenotriphosphate of Formula (I) or pharmaceutically acceptable salt thereof, the process comprising:

(a) forming a mixture comprising salicyl phosphorochloridite and pyrophosphate to provide a cyclic phosphite intermediate;

(b) reacting the cyclic phosphite intermediate with a nucleoside to provide a nucleoside phosphite intermediate;

(c) oxidizing the nucleoside phosphite intermediate with 3H-1,2-benzothaselenol-3-one; and (d) hydrolyzing the oxidized nucleoside phosphate intermediate;

wherein the nucleoside 5'-α-P-selenotriphosphate has a structure of Formula (I):

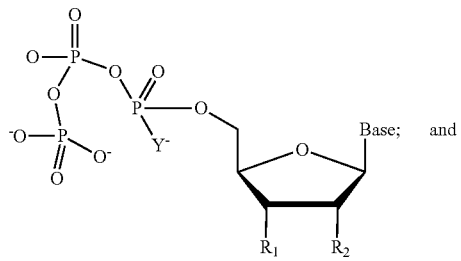

Formula (I)

$R_1$ and $R_2$ each are independently selected from H and OH;

Y is Se; and

Base is 9-adeninyl, 1-cytosinyl, 9-guaninyl, 1-thyminyl, 1-uracilyl, or a modified nucleobase of Formula (III):

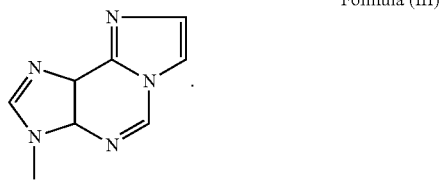

Formula (III)

2. The process of claim 1, wherein:

$R_1$ is OH; and $R_2$ is H.

3. The process of claim 1, wherein a reaction temperature of steps (a) and (b) are each independently in a range from about 0° C. to about 100° C.

4. The process of claim 1, wherein said process is a one-pot reaction.

5. The process of claim 1, wherein said process does not comprise protection or deprotection of any nucleoside functional group.

6. The process of claim 1, wherein an isolated yield of the nucleoside 5'-α-P-selenotriphosphate is from about 80% to about 100%.

7. The process of claim 1, wherein said nucleoside 5'-α-P-selenotriphosphate is synthesized according to Scheme D:

Scheme D

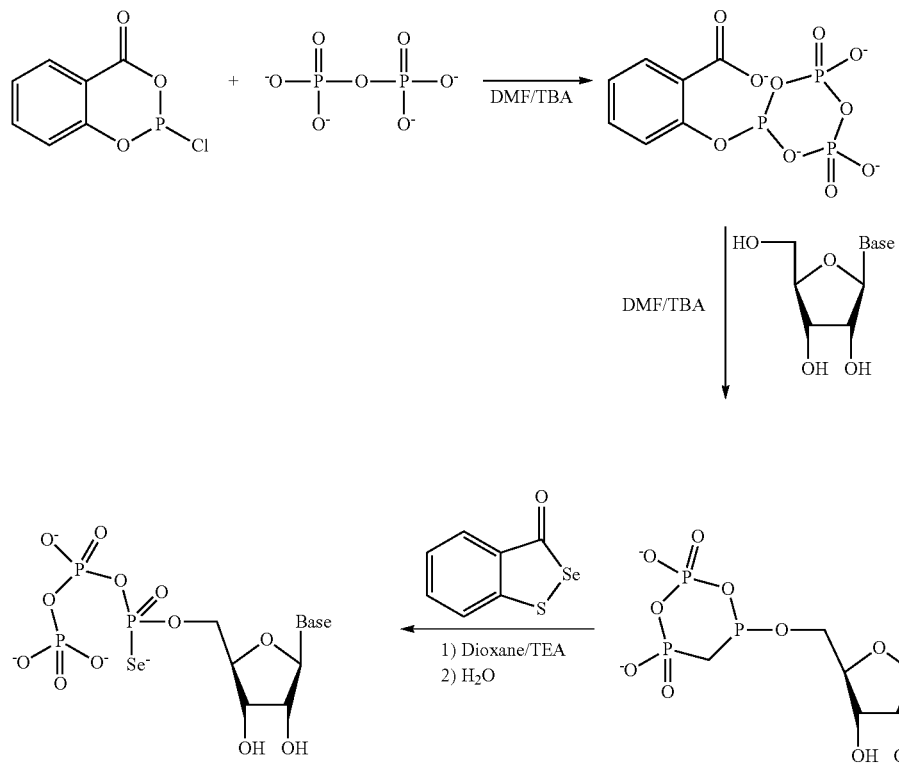

8. The process of claim 1, wherein step (a) comprises forming a mixture of tributylammonium pyrophosphate and salicyl phosphochloridite in dimethylformamide.

9. The process of claim 1, wherein step (d) consists of adding water to the mixture and stirring.

10. A process of preparing a nucleoside 5'-triphosphate of Formula (I) or pharmaceutically acceptable salt thereof, the process comprising:
(a) reacting salicyl phosphorochloridite with pyrophosphate to provide a cyclic phosphite intermediate;
(b) reacting the cyclic phosphite intermediate with a nucleoside to provide a nucleoside phosphite intermediate;
(c) oxidizing the nucleoside phosphite intermediate; and
(d) hydrolyzing the oxidized nucleoside phosphate intermediate;
wherein the nucleoside 5'-triphosphate has a structure of Formula (I):

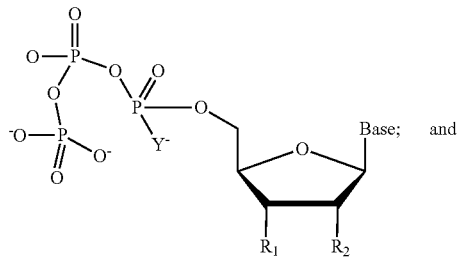

Formula (I)

and $R_1$ and $R_2$ each are independently selected from H and OH;
Y is O; and
Base is 9-adeninyl, 1-cytosinyl, 9-guaninyl, 1-thyminyl, 1-uracilyl, or a modified nucleobase of Formula (III):

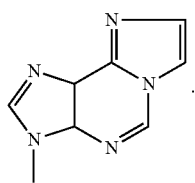

Formula (III)

11. The process of claim 10, wherein:
$R_1$ is OH; and
$R_2$ is H.

12. The process of claim 10, wherein a reaction temperature of steps (a) and (b) are each independently in a range from about 0° C. to about 100° C.

13. The process of claim 10, wherein said process is a one-pot reaction.

14. The process of claim 10, wherein said process does not comprise protection or deprotection of any nucleoside functional group.

15. The process of claim 10, wherein an isolated yield of the nucleoside 5'-triphosphate is from about 80% to about 100%.

16. The process of claim 10, wherein the nucleoside triphosphate is synthesized according to Scheme B: